(12) United States Patent
Ronsheim et al.

(10) Patent No.: US 7,501,438 B2
(45) Date of Patent: Mar. 10, 2009

(54) PYRIDOIMIDAZOLE DERIVATIVES

(75) Inventors: Matthew Ronsheim, Port Jefferson, NY (US); Gian-Luca Araldi, East Setauket, NY (US)

(73) Assignee: Forest Laboratories Holdings Limited (BM)

( * ) Notice: Subject to any disclaimer, the term of this patent is extended or adjusted under 35 U.S.C. 154(b) by 0 days.

(21) Appl. No.: 11/772,270

(22) Filed: Jul. 2, 2007

(65) Prior Publication Data

US 2008/0009491 A1 Jan. 10, 2008

Related U.S. Application Data

(60) Provisional application No. 60/806,746, filed on Jul. 7, 2006.

(51) Int. Cl.
| | |
|---|---|
| A01N 43/42 | (2006.01) |
| A61K 31/44 | (2006.01) |
| C07D 471/02 | (2006.01) |
| C07D 491/02 | (2006.01) |
| C07D 498/02 | (2006.01) |
| C07D 513/02 | (2006.01) |
| C07D 515/02 | (2006.01) |

(52) U.S. Cl. ........................ 514/300; 546/121
(58) Field of Classification Search ................. 546/121; 514/300
See application file for complete search history.

(56) References Cited

U.S. PATENT DOCUMENTS

| | | | | |
|---|---|---|---|---|
| 4,882,327 A | * | 11/1989 | King | 514/213.01 |
| 4,988,698 A | | 1/1991 | Kato et al. | |
| 5,260,303 A | * | 11/1993 | Becker et al. | 514/30 |
| 5,434,161 A | * | 7/1995 | Becker et al. | 514/300 |
| 5,523,318 A | | 6/1996 | Larsen et al. | |
| 5,565,468 A | | 10/1996 | Larsen et al. | |
| 6,207,693 B1 | | 3/2001 | Setoi et al. | |
| 6,743,919 B2 | | 6/2004 | Koya et al. | |
| 6,838,456 B2 | | 1/2005 | Orme et al. | |
| 2007/0015771 A1 | | 1/2007 | Matteucci et al. | |
| 2007/0037974 A1 | * | 2/2007 | Brotherton-Pleiss et al. | 544/120 |
| 2007/0043057 A1 | * | 2/2007 | Matteucci et al. | 514/252.04 |

FOREIGN PATENT DOCUMENTS

| | | | |
|---|---|---|---|
| WO | WO 92/15593 | | 9/1992 |
| WO | 9308187 | * | 4/1993 |
| WO | WO 93/08187 | | 4/1993 |
| WO | WO 93/13099 | | 7/1993 |
| WO | WO 93/25553 | | 12/1993 |
| WO | WO 03/022274 | | 3/2003 |
| WO | 2005/113553 | * | 12/2005 |
| WO | WO 2005/113553 | | 12/2005 |
| WO | WO 2005/113553 A2 | | 12/2005 |
| WO | WO 2006/015263 | | 2/2006 |
| WO | WO 2006/024517 | | 3/2006 |
| WO | WO 2008/085302 | | 7/2008 |

OTHER PUBLICATIONS

Coutts et al., Current Opinion in Pharmacology (2004), 4(6), 572-579.*
Becker et al., Journal of Medicinal Chemistry (2006), 49(3), 1125-1139.*
Anderson et al., Journal of Heterocyclic Chemistry (1995), 32(5), 1525-30.*
Kolar et al., Journal of Heterocyclic Chemistry (1991), 28(7), 1715-20.*
Bermudez et al., Journal of Medicinal Chemistry (1990), 33(7), 1924-9.*
Edgar et al., Journal of Organic Chemistry (1979), 44(3), 396-400.*
Di Marzo et al., Endocannabinoids: Endogenous Cannabinoid Receptor Ligands with Neuromodulatory Action, Trends Neurosci., vol. 21, No. 12, 521-528, 1998.
Pertwee, Roger G., Pharmacology of Cannabinoid CB1 and CB2 Receptors, Pharmacol. Ther., vol. 74, No. 2, 129-180, 1997.
International Search Report for PCT/US2007/072621, mailed Aug. 19, 2008.
Written Opinion of the International Searching Authority for PCT/US2007/072621, mailed Aug. 19, 2008.
Anderson et al., The Reaction of Imidazo[1,5a]pyridines with methyl-and Phyenyltriazolinediones and diethyl azodicarboxylete, Journal of Heterocyclic Chemistry, 1995, vol. 32, pp. 1525-1530.
Kolar et al., Heterocycles from Amino Acids. A Novel Synthetic approach for Imidazo[1,5-a]pyridines and Imidazo[1,5-a]quinolines, Journal of Heterocyclic Chemistry, 1991, vol. 28, pp. 1715-1720.
Anderson et al., The Reaction of Imidazol [1,5-α]pyridines with Methyl-and Phenyltriazolinediones and with Diethyl Azodicarboxylate, J. Heterocyclic Chem., 32, 1525, (1995).
Becker, et al., Pyrrolizidine Esters and Amides as 5-HT$_4$ Receptor Agonists and Antagonists, J. Med. Chem., 2006, 49, 1125-1139.
Bermudez et al., 5-Hydroxytryptamine (5-HT$_3$) Receptor Antagonists. 1. Indazole and Indolizine-3-carboxylic Acid Derivatives, J. Med. Chem., 1990, 33, 1924-1929.
Durant, et al., Potential Histamine H$_2$-Receptor Antagonists. 1. Aminoethylimidazo[1,2-α]pyridines and -Imidazo[1,5-α]pyridines, Journal of Medicinal Chemistry, 1973, vol. 16, No. 11, 1272-1276.

(Continued)

*Primary Examiner*—D. Margaret Seaman
*Assistant Examiner*—Niloofar Rahmani
(74) *Attorney, Agent, or Firm*—Michael Ciraolo, Esq.; Jonathan Paul Mitchell

(57) ABSTRACT

The present invention relates to pyridoimidazole derivatives that act as cannabinoid receptor ligands, e.g., CB2 ligands. The invention also relates to methods of preparing the compounds, compositions containing the compounds, and to methods of treatment using the compounds.

24 Claims, No Drawings

OTHER PUBLICATIONS

Edgar et al., Synthesis of L-(5-Chloro-2-pyridyl)glycine, J. Org. Chem., vol. 44, No. 3, 1979, 396-400.

Kolar et al., Heterocycles from Amino Acids. A Novel Synthetic Approach for Imidazo[1,5-α]pyridines and Imidazol[1,5-α]quinolines, J. Heterocyclic Chem. 28, 1715 (1991), 1715-1720.

Sawada, et al., 4-(Benzoylindolizinyl)butryric Acids; Novel Nosteroidal Inhibitors of Steroid 5α-Reductase. III., Chem. Pharm. Bull., 49(7) 799-813 (2001).

Wang et al., Convenient Preparation of Novel Class of Imidazol [1,5-α]pyridines: Decisive Role by Ammonium Acetate in Chemoselectivity, J. Org. Chem., 2003, 68, 5415-5418.

* cited by examiner

PYRIDOIMIDAZOLE DERIVATIVES

This application claims the benefit of U.S. Provisional Application Ser. No. 60/806,746, filed Jul. 7, 2006, the entire disclosure of which is hereby incorporated by reference.

FIELD OF THE INVENTION

The present invention relates to pyridoimidazole derivatives that act as cannabinoid receptor ligands, e.g., CB2 ligands. The invention also relates to methods of preparing the compounds, compositions containing the compounds, and to methods of treatment using the compounds.

BACKGROUND OF THE INVENTION

Cannabinoids are a specific class of psychoactive compounds present in *Cannabis sativa*. Cannabinoids are known to affect various systems and/or organs, the most important being the central nervous system and the cardiovascular system. Effects of cannabinoid intake include alterations in memory and cognition, euphoria and sedation. Cannabinoids also increase heart rate and vary systemic arterial pressure. Peripheral effects related to bronchial constriction, immunomodulation, and inflammation have also been observed. The ability of cannabinoids to reduce intraocular pressure and to affect respiratory and endocrine systems is also well known.

There are two main types of cannabinoid receptors, CB1 which is expressed mainly in the basal ganglia and the limbic system of the brain, the lungs, liver and kidneys and CB2 which is mainly expressed on T cells of the immune system and in hematopoietic cells.

Compounds that are agonists or antagonists of one or both of the cannabinoid receptors have been shown to provide a variety of pharmacological effects. See, e.g., Pertwee, R. G., PHARMACOL. THER., 74:129-180 (1997) and Di Marzo, V., TRENDS NEUROSCI., 21:521-528 (1998). For example, cannabinoid receptor ligands have been shown to have pharmacological effects on the central nervous system, the immune system and the endocrine system. Consequently, there is considerable need to develop compounds that act as cannabinoid receptor (e.g., CB2 receptor) ligands.

SUMMARY OF INVENTION

The present invention relates to pyridoimidazole derivatives that act as cannabinoid receptor ligands, e.g., CB2 ligands. The invention also relates to methods of preparing the compounds, compositions containing the compounds, and to methods of treatment using the compounds.

DETAILED DESCRIPTION OF THE INVENTION

In one aspect, the present invention relates to compounds of formula I:

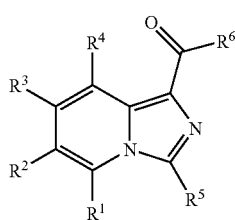

(I)

wherein
$R^1$, $R^2$, $R^3$ and $R^4$ are each independently hydrogen, halogen, hydroxyl, cyano, nitro, amino, alkylamino, dialkylamino, carboxyl, alkyl, alkenyl, alkynyl, aryl, arylalkyl, heteroaryl, heteroarylalkyl, heterocycle, heterocyclealkyl, cycloalkyl, aroyl, acyl, alkoxy, aryloxy, alkylthio, arylthio, alkoxycarbonyl or aryloxycarbonyl;

$R^5$ is alkyl, aryl or heterocyclealkyl;

$R^6$ is hydroxyl, alkyl, halogenated alkyl, alkenyl, alkynyl, alkoxy, aryloxy, aryl, arylalkyl, heteroaryl, heteroarylalkyl, heterocycle, heterocyclealkyl or $NR^7R^8$;

$R^7$ and $R^8$ are each independently, hydrogen, alkyl, aryl, cycloalkyl, cycloalkylalkyl, arylalkyl, heteroaryl, heteroarylalkyl, heterocycle, or heterocyclealkyl;

and pharmaceutically acceptable salts or solvates (e.g., hydrates) thereof, or solvates of pharmaceutically acceptable salts thereof;

with the provisos that:

(i) when $R^6$ is $OCH_3$, then $R^5$ is other than methyl, phenyl, chlorophenyl, fluorophenyl, methoxyphenyl, hydroxyphenyl or nitrophenyl;

(ii) $R^6$ is other than 1-methyl-2-[4-(2-pyrimidinyl)-1-piperazinyl]ethyl;

(iii) when $R^6$ is 2-pyridinyl, then $R^5$ is other than phenyl, chlorophenyl, fluorophenyl, nitrophenyl, methoxyphenyl or alkyl substituted phenyl;

(iv) when $R^5$ is alkyl, $R^6$ is $NR^7R^8$ and one of $R^7$ and $R^8$ is hydrogen, then the other of $R^7$ and $R^8$ is not hexahydropyrrolizinylmethyl, hexahydro-1H-2,5-methanocyclopenta[c]pyrrolyl, azabicyclo[2.2.2]oct-3-yl, 8-methyl-8-azabicyclo[3.2.1]-oct-3-yl or 9-methyl-9-azabicyclo[3.2.1]-non-3-yl;

(v) when $R^6$ is OH or OEt, then $R^5$ is other than phenyl, ethyl, $CF_3$, or isobutyl, and said compound is not
2,2,2-trifluoro-1-[3-(4-nitrophenyl)imidazo[1,5-a]pyridine-1-yl-ethanone,
phenyl(3-phenylimidazo[1,5-a]pyridine-1-yl-methanone,
1-[3-(4-chlorophenyl)imidaz[1,5-a]pyridine-1-yl]-1-propanone, or
1-(3-methylimidazo[1,5-a]pyridine-1-yl)ethanone.

In another aspect, the present invention relates to compounds of formula I:

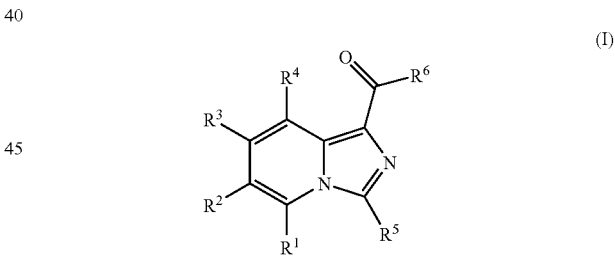

(I)

wherein
$R^1$, $R^2$, $R^3$ and $R^4$ are each hydrogen;
$R^5$ is alkyl, aryl or heterocyclealkyl;
$R^6$ is hydroxyl, alkyl, halogenated alkyl, aryl, heterocycle, or $NR^7R^8$;
$R^7$ and $R^8$ are each independently, hydrogen, alkyl, cycloalkyl, aryl, arylalkyl, heteroaryl, heteroarylalkyl, or heterocycle;

and pharmaceutically acceptable salts or solvates (e.g., hydrates) thereof, or solvates of pharmaceutically acceptable salts thereof;

with the provisos that:

(i) $R^6$ is other than 1-methyl-2-[4-(2-pyrimidinyl)-1-piperazinyl]ethyl;

(ii) when $R^5$ is alkyl, $R^6$ is $NR^7R^8$ and one of $R^7$ and $R^8$ is hydrogen, then the other of $R^7$ and $R^8$ is not hexahydro-1H-

2,5-methanocyclopenta[c]pyrrolyl, azabicyclo[2.2.2]oct-3-yl, 8-methyl-8-azabicyclo[3.2.1]-oct-3-yl or 9-methyl-9-azabicyclo[3.2.1]-non-3-yl;

(iii) when $R^6$ is OH, then $R^5$ is other than phenyl, ethyl, $CF_3$ or iso-butyl, and said compound is not 2,2,2-trifluoro-1-[3-(4-nitrophenyl)imidazo[1,5-a]pyridine-1-yl-ethanone, phenyl(3-phenylimidazo[1,5-a]pyridine-1-yl-methanone, 1-[3-(4-chlorophenyl)imidaz[1,5-a]pyridine-1-yl]-1-propanone, or 1-(3-methylimidazo[1,5-a]pyridine-1-yl)ethanone.

In another aspect, the present invention relates to compounds of formula I:

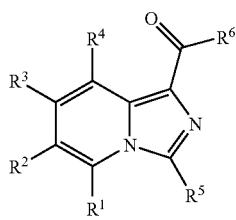

(I)

wherein:

$R^1$, $R^2$, $R^3$ and $R^4$ are each independently hydrogen, halogen, hydroxyl, cyano, nitro, amino, carboxyl, alkyl, alkenyl, or aryl;

$R^5$ is alkyl, naphthalene, or —$(CH_2)_n$-A, $R^6$ is alkyl, $CF_3$, hydroxyl, naphthalene, A, —NH—$(CH_2)_m$-A, —N($CH_3$)$(CH_2)_m$-A, —NH—$(CH_2)_m$—B, or —N($CH_3$)$(CH_2)_m$—B;

n=1, 2 or 3;

m=0, 1, 2 or 3;

A is represented by:

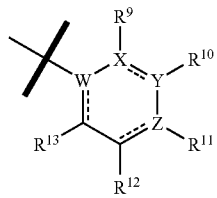

wherein each ----- independently represents a single or double bond;

$R^9$, $R^{10}$, $R^{11}$, $R^{12}$ and $R^{13}$ are each independently H, halogen, alkyl or $NO_2$, W, X, Y and Z are each independently C, O or N; and B is selected norborane, naphthalene, adamantane or 1,3-dimethyl adamantane;

and pharmaceutically acceptable salts or solvates (e.g., hydrates) thereof, or solvates of pharmaceutically acceptable salts thereof;

with the provisos that:

when $R^5$ is —$(CH_2)_n$-A and A is optionally substituted phenyl, then n is other than 1;

when $R^6$ is hydroxyl and $R^1$—$R^4$ are hydrogen, then $R^5$ is other than ethyl, iso-butyl or $CF_3$;

and said compound is not 1-(3-methylimidazo[1,5-a]pyridine-1-yl)ethanone.

In another aspect, the present invention provides a compound according to formula II:

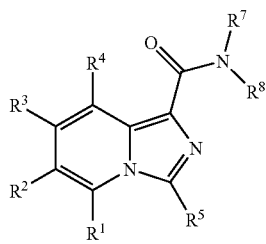

(II)

wherein $R^1$ through $R^4$ are each independently hydrogen, halogen, hydroxy, cyano, nitro, amino, carboxyl, alkyl, alkenyl, or aryl;

$R^5$ is hydrogen, alkyl, naphthalene or —$(CH_2)_n$-A, wherein n=0, 1, 2 or 3;

$R^7$ and $R^8$ are each individually hydrogen, alkyl, naphthalene, A, B, -alkylene-A or -alkylene-B;

wherein A is represented by:

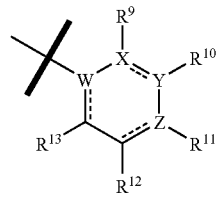

wherein each ----- independently represents a single or double bond;

$R^9$ through $R^{13}$ are each independently hydrogen, halogen, alkyl or $NO_2$, W, X, Y, and Z are each independently C, O and N; and B is norborane, naphthalene, adamantane and 1,3-dimethyl adamantane;

and pharmaceutically acceptable salts or solvates (e.g., hydrates) thereof, or solvates of pharmaceutically acceptable salts thereof;

with the proviso that $R^5$ is other than 4-trifluoromethyl-3-pyridinyl.

In one embodiment, when $R^6$ is OH or OEt, then $R^5$ is other than phenyl, ethyl, $CF_3$, or butyl. In another embodiment, when $R^6$ is OH, $R^5$ is other than isobutyl. In another embodiment, when $R^6$ is OH, $R^5$ is other than butyl. In another embodiment, when $R^6$ is OH, $R^5$ is other than alkyl. In another embodiment, when $R^6$ is hydroxyl, then $R^5$ is other than ethyl, butyl or $CF_3$.

In one embodiment $R^1$, $R^2$, $R^3$ and $R^4$ are independently hydrogen, halogen, hydroxy, cyano, nitro, amino, carboxyl, alkyl, alkenyl, or aryl. In a further embodiment $R^1$, $R^2$, $R^3$ and $R^4$ are hydrogen.

In further embodiments, $R^5$ is aryl (e.g., naphthalenyl), alkyl (e.g., butyl, propyl) or heterocyclealkyl (e.g., morpholinylethyl, such as 2-morpholin-4-yl-ethyl)

In additional embodiments, $R^6$ is hydroxyl, alkyl (e.g., propyl), halogenated alkyl (e.g., $CF_3$), aryl (e.g., optionally substituted phenyl, optionally substituted naphthalenyl), heterocycle (e.g., optionally substituted morpholino) or $NR^7R^8$;

In certain embodiments, $R^7$ and $R^8$ are each independently, hydrogen, alkyl (e.g., methyl), cycloalkyl (e.g., bicyclo[2.2.1]heptyl, adamantanyl, 3,5-dimethyl-tricyclo[3.3.1.1$^{3,7}$]decanyl), aryl (e.g., optionally substituted phenyl, optionally substituted naphthalenyl), arylalkyl (e.g., optionally substituted benzyl), heteroaryl (e.g., optionally substituted pyridinyl), heteroarylalkyl (e.g., optionally substituted pyridinylmethyl), or heterocycle (e.g., optionally substituted piperidinyl).

For example, $R^6$ may be hydroxyl, unsubstituted alkyl (such as propyl), substituted alkyl (such as CF$_3$), iodophenyl (e.g., 2-iodophenyl), naphthalenyl (e.g., naphthalene-1-yl), —NH-adamantan-1-yl, iodonitrophenyl (e.g., 2-iodo-5-nitrophenyl), —NH-piperidinyl, —NH-chlorophenyl (e.g., —NH-3-chlorophenyl), morpholinyl (e.g., morpholin-4-yl), —NH-chlorobenzyl (e.g., —NH-4-chlorobenzyl), —N(CH$_3$)phenyl, —NH-bicyclo[2.2.1]heptyl (e.g., —NH-bicyclo[2.2.2]hept-2-yl), —NH-fluorophenyl (e.g., —NH-3-fluorophenyl), —NH-pyridinyl (e.g., —NH-3-pyridinyl), —NH-pyridinylmethyl (e.g., —NH-2-pyridinylmethyl), —NH-naphthalenyl (e.g., —NH-naphthalene-1-yl), —NH-3,5-dimethyl-tricyclo[3.3.1.1$^{3,7}$]decanyl (e.g., —NH-3,5-dimethyl-tricyclo[3.3.1.1$^{3,7}$]decan-1-yl), —NH-phenyl, or —NH-benzyl.

In one embodiment, each of W, X, Y and Z are C. In another embodiment, one of W, X, Y and Z is N and the remainder are C (e.g., W is N and X, Y and Z are C). In a further embodiment, W is N, X and Y are C and Z is O.

In one embodiment, each ---- represents a single bond. In another embodiment, each ----- represents a double bond.

In certain embodiments, the compound of formula I is selected from the following sub formulae:

(Ia) $R^1$-$R^4$ are hydrogen,
$R^5$ is aryl (e.g., naphthalenyl),
$R^6$ is hydroxyl, alkyl (e.g. propyl), halogenated alkyl (e.g., CF$_3$), optionally substituted aryl (e.g., iodophenyl) or NR$^7$R$^8$, and
$R^7$ and $R^8$ are independently hydrogen or cycloalkyl (e.g., adamantanyl);

(Ib) $R^1$-$R^4$ are hydrogen,
$R^5$ is alkyl (e.g., propyl, butyl),
$R^6$ is hydroxyl, halogenated alkyl (e.g., CF$_3$), optionally substituted aryl (e.g., optionally substituted naphthalenyl or optionally substituted phenyl (such as iodophenyl, iodonitrophenyl)) or NR$^7$R$^8$,
$R^7$ and $R^8$ are independently hydrogen or cycloalkyl (e.g., adamantanyl);

(Ic) $R^1$-$R^4$ are hydrogen,
$R^5$ is heterocyclealkyl (e.g., morpolinylethyl),
$R^6$ is halogenated alkyl (e.g., CF$_3$), optionally substituted aryl (e.g., optionally substituted naphthalenyl or optionally substituted phenyl (such as iodophenyl)), heteroaryl (e.g., pyridinyl), heterocycle (e.g., morpholinyl) or NR$^7$R$^8$,
$R^7$ and $R^8$ are independently hydrogen, alkyl (e.g., methyl), optionally substituted aryl (e.g., optionally substituted naphthalenyl or optionally substituted phenyl (such as phenyl, fluorophenyl, iodophenyl, chlorophenyl)), cyclooalkyl (e.g., adamantanyl, 3,5-dimethyl-tricyclo[3.3.1.1$^{3,7}$]decanyl), heterocycle (e.g., piperidinyl), arylalkyl (e.g., optionally substituted benzyl, e.g., chlorobenzyl), heteroarylalkyl (e.g., optionally substituted pyridinylmethyl).

In certain embodiments, the compound of formula I is selected from:
1-(3-naphthalen-1-yl-imidazo[1,5-a]pyridin-1-yl)-butan-1-one,
(2-iodo-phenyl)-(3-naphthalen-1-yl-imidazo[1,5-a]pyridin-1-yl)-methanone,
2,2,2-trifluoro-1-(3-naphthalen-1-yl-imidazo[1,5-a]pyridin-1-yl)-ethanone,
3-naphthalen-1-yl-imidazo[1,5-a]pyridine-1-carboxylic acid,
3-naphthalen-1-yl-imidazo[1,5-a]pyridine-1-carboxylic acid adamantan-1-ylamide,
3-butyl-imidazo[1,5-a]pyridin-1-yl-naphthalen-1-yl-methanone,
(3-butyl-imidazo[1,5-a]pyridin-1-yl)-(2-iodo-phenyl)-methanone,
3-butyl-imidazo[1,5-a]pyridin-1-yl)-2(2-iodo-5-nitro-phenyl)-methanone,
1-(3-butyl-imidazo[1,5-a]pyridin-1-yl)-2,2,2-trifluoro-ethanone,
3-butyl-imidazo[1,5-a]pyridine-1-carboxylic acid,
3-butyl-imidazo[1,5-a]pyridine-1-carboxylic acid adamantan-1-ylamide,
3-propyl-imidazo[1,5-a]pyridin-1-yl-naphthalen-1-yl-methanone,
(2-iodo-phenyl)-(3-propyl-imidazo[1,5-a]pyridin-1-yl)-methanone,
2,2,2-trifluoro-1-(3-propyl-imidazo[1,5-a]pyridin-1-yl)-ethanone,
3-propyl-imidazo[1,5-a]pyridine-1-carboxylic acid,
3-propyl-imidazo[1,5-a]pyridine-1-carboxylic acid adamantan-1-ylamide,
[3-(2-morpholin-4-yl-ethyl)-imidazo[1,5-a]pyridin-1-yl]-naphthalen-1-yl-methanone,
(2-iodo-phenyl)-[3-(2-morpholin-4-yl-ethyl)-imidazo[1,5-a]pyridin-1-yl]-methanone,
2,2,2-trifluoro-1-[3-(2-morpholin-4-yl-ethyl)-imidazo[1,5-a]pyridin-1-yl]-ethanone,
3-(2-morpholin-4-yl-ethyl)-imidazo[1,5-a]pyridine-1-carboxylic acid adamantan-1-ylamide,
3-(2-morpholin-4-yl-ethyl)-imidazo[1,5-a]pyridine-1-carboxylic acid piperidin-1-ylamide,
3-(2-morpholin-4-yl-ethyl)-imidazo[1,5-a]pyridine-1-carboxylic acid (3-chloro-phenyl)-amide,
morpholin-4-yl-[3-(2-morpholin-4-yl-ethyl)-imidazo[1,5-a]pyridin-1-yl]-methanone,
3-(2-morpholin-4-yl-ethyl)-imidazo[1,5-a]pyridine-1-carboxylic acid 4-chloro-benzylamide,
3-(2-morpholin-4-yl-ethyl)-imidazo[1,5-a]pyridine-1-carboxylic acid methyl-phenyl-amide,
3-(2-morpholin-4-yl-ethyl)-imidazo[1,5-a]pyridine-1-carboxylic acid bicyclo[2.2.1]hept-2-ylamide,
3-(2-morpholin-4-yl-ethyl)-imidazo[1,5-a]pyridine-1-carboxylic acid (3-fluoro-phenyl)-amide,
3-(2-morpholin-4-yl-ethyl)-imidazo[1,5-a]pyridine-1-carboxylic acid pyridin-3-ylamide,
3-(2-morpholin-4-yl-ethyl)-imidazo[1,5-a]pyridine-1-carboxylic acid (pyridin-3-ylmethyl)-amide,
3-(2-morpholin-4-yl-ethyl)-imidazo[1,5-a]pyridine-1-carboxylic acid naphthalen-1-ylamide,
3-(2-morpholin-4-yl-ethyl)-imidazo[1,5-a]pyridine-1-carboxylic acid (3,5-dimethyl-tricyclo[3.3.1.1$^{3,7}$]decan-1-yl)-amide,
3-(2-morpholin-4-yl-ethyl)-imidazo[1,5-a]pyridine-1-carboxylic acid phenylamide, and
3-(2-morpholin-4-yl-ethyl)-imidazo[1,5-a]pyridine-1-carboxylic acid benzylamide,
wherein free base forms listed above can also be in the form of a pharmaceutically acceptable salt wherein a compound listed above (in either a free base form or in the form of a pharmaceutically acceptable salt) can also be in the form of a solvate (such as a hydrate), wherein a compound listed above (in a free base form or solvate thereof, or in the form of a pharmaceutically acceptable salt or solvate thereof) can also be in the form of a polymorph, and wherein if the compound exhibits chirality it can be in the form of a mixture of enantiomers such as a racemate or a mixture of diastereomers, or can be in the form of a single enantiomer or a single diastereomer.

As used herein the term "halogen" means F, Cl, Br, and I.

The term "alkyl" means a substituted or unsubstituted saturated hydrocarbon radical which may be straight-chain or branched-chain and may comprise about 1 to about 20 carbon atoms, for instance 1 to 12 carbon atoms, such as 1 to 8 carbon atoms, e.g., 1 to 4 carbon atoms. Suitable alkyl groups include, but are not limited to, methyl, ethyl, propyl, isopropyl, butyl, sec-butyl, tert-butyl, pentyl, hexyl, heptyl, octyl, nonyl, decyl, undecyl, and dodecyl. Other examples of suitable alkyl groups include, but are not limited to, 1-, 2- or 3-methylbutyl, 1,1-, 1,2- or 2,2-dimethylpropyl, 1-ethylpropyl, 1-, 2-, 3- or 4-methylpentyl, 1,1-, 1,2-, 1,3-, 2,2-, 2,3- or 3,3-dimethylbutyl, 1- or 2-ethylbutyl, ethylmethylpropyl, trimethylpropyl, methylhexyl, dimethylpentyl, ethylpentyl, ethylmethylbutyl, dimethylbutyl, and the like.

Substituted alkyl groups are alkyl groups as described above which are substituted in one or more positions by, e.g., halogen, hydroxyl, amino, alkylamino, dialkylamino, aryl, heteroaryl, alkoxy, nitro and cyano, and combinations thereof.

The term "halogenated alkyl" means a saturated hydrocarbon radical which may be straight-chain or branched-chain and may comprise about 1 to about 20 carbon atoms, for instance 1 to 12 carbon atoms, such as 1 to 8 carbon atoms, e.g., 1 to 4 carbon atoms, that is substituted by one or more halogens, such as, but not limited to, $-CF_3$, $CF_2CF_3$, $CHF_2$, $CH_2F$, and the like. The use of the term "halogenated alkyl" should not be construed to mean that a "substituted alkyl" group may not be substituted by one or more halogens.

The term "alkenyl" means a substituted or unsubstituted hydrocarbon radical which may be straight-chain or branched-chain, which contains one or more carbon-carbon double bonds, and which may comprise about 1 to about 20 carbon atoms, such as 1 to 12 carbon atoms, for instance 1 to 6 carbon atoms. Suitable alkenyl groups include ethenyl, propenyl, butenyl, etc.

Substituted alkenyl groups are alkenyl groups as described above which are substituted in one or more positions by, e.g., halogen, hydroxyl, amino, carboxy, alkylamino, dialkylamino, aryl, heteroaryl, alkoxy, nitro and cyano, and combinations thereof.

The term "alkylene" means a linear saturated divalent hydrocarbon radical of one to six carbon atoms or a branched saturated divalent hydrocarbon radical of three to six carbon atoms unless otherwise stated e.g., methylene, ethylene, propylene, 1-methylpropylene, 2-methylpropylene, butylene, pentylene, and the like.

The term "alkynyl" means a substituted or unsubstituted aliphatic hydrocarbon radical which may be straight-chain or branched-chain and which contains one or more carbon-carbon triple bonds. Preferably the alkynyl group contains 2 to 15 carbon atoms, such as 2 to 12 carbon atoms, e.g., 2 to 8 carbon atoms. Suitable alkynyl groups include ethynyl, propynyl, butynyl, etc.

Substituted alkynyl groups are alkynyl groups as described above which are substituted in one or more positions by, e.g., halogen, hydroxyl, amino, carboxy, alkylamino, dialkylamino, aryl, heteroaryl, alkoxy, nitro and cyano, and combinations thereof.

The term "amino" means $-NH_2$.

The term "alkylamino" means $-NH(alkyl)$, wherein alkyl is as described above.

The term "dialkylamino" means $-N(alkyl)_2$, wherein alkyl is as described above.

The term "aryl" means a substituted or unsubstituted aromatic monocyclic or bicyclic ring system comprising about 5 to about 14 carbon atoms, e.g., about 6 to about 10 carbon atoms. Suitable aryl groups include, but are not limited to, phenyl, naphthyl, anthracenyl.

Substituted aryl groups include the above-described aryl groups which are substituted one or more times by, for example, but not limited to, halogen, hydroxyl, amino, carboxy, alkylamino, dialkylamino, aryl, heteroaryl, alkoxy, nitro and cyano, and combinations thereof.

The term "arylamino" means $-NH(aryl)$, wherein aryl is as described above.

The term "diarylamino" means $-N(aryl)_2$, wherein aryl is as described above.

The term "amido" means $-CONH_2$.

The term "arylalkyl" refers to an -(alkylene)-aryl group in which the aryl and alkylene portions are in accordance with the previous descriptions. Suitable examples include, but are not limited to, benzyl, 1-phenethyl, 2-phenethyl, phenpropyl, phenbutyl, phenpentyl, and napthylmethyl.

The term "carboxyl" means $-C(O)OH$.

The term "cycloalkyl" means a monocyclic, bicyclic or tricyclic nonaromatic saturated hydrocarbon radical having 3 to 10 carbon atoms, such as 3 to 8 carbon atoms, for example, 3 to 6 carbon atoms. Suitable cycloalkyl groups include, but are not limited to, cyclopropyl, cyclobutyl, cyclopentyl, cyclohexyl, cycloheptyl, cyclooctyl, norbornyl, 1-decalin, adamant-1-yl, and adamant-2-yl. Other suitable cycloalkyl groups include, but are not limited to, spiropentyl, bicyclo[2.1.0]pentyl, bicyclo[3.1.0]hexyl, spiro[2.4]heptyl, spiro[2.5]octyl, bicyclo[5.1.0]octyl, spiro[2.6]nonyl, bicyclo[2.2.0]hexyl, spiro[3.3]heptyl, bicyclo[4.2.0]octyl, and spiro[3.5]nonyl. Preferred cycloalkyl groups include cyclopropyl, cyclobutyl, cyclopentyl and cyclohexyl. The cycloalkyl group can be substituted, for example, by one or more halogens and/or alkyl groups.

The term "cycloalkylalkyl" means a -(alkylene)-cycloalkyl in which the cycloalkyl group is as previously described; e.g., cyclopropylmethyl, cyclobutylmethyl, cyclopentylethyl, or cyclohexylmethyl, and the like.

The term "heteroaryl" means a substituted or unsubstituted aromatic monocyclic or multicyclic ring system comprising 5 to 14 ring atoms, preferably about 5 to about 10 ring atoms and most preferably 5 or 6 ring atoms, wherein at least one of the ring atoms is an N, O or S atom. Suitable heteroaryl groups include, but are not limited to furyl, thienyl, pyrrolyl, pyrazolyl, imidazolyl, pyridyl, pyrimidinyl, benzimidazolyl, indazolyl, indolyl, quinolinyl, isoquinolinyl, naphthyridinyl and the like.

Substituted heteroaryl groups include the above-described heteroaryl groups which are substituted one or more times by, for example, but not limited to, halogen, hydroxyl, amino, carboxy, alkylamino, dialkylamino, aryl, heteroaryl, alkoxy, nitro and combinations thereof.

The term "heteroarylalkyl" refers to a -(alkylene)-heteroaryl group wherein the heteroaryl and alkylene portions are in accordance with the previous discussions. Suitable examples include, but are not limited to, pyridylmethyl, thiazolylmethyl, thienylmethyl, pyrimidinylmethyl, pyrazinylmethyl, and isoquinolinylmethyl, and the like.

The term "heterocycle" means a substituted or unsubstituted non-aromatic mono- or multicyclic ring system comprising 3 to 10 atoms, preferably 5 or 6, wherein at least one of the ring atoms is an N, O or S atom. Suitable heterocycle groups include, but are not limited to tetrahydrofuranyl, tetrahydrothienyl, tetrahydropyranyl, dihydropyranyl, pyrrolidinyl, piperidinyl, piperazinyl, thiomorpholinyl, morpholinyl, isoxazolinyl, and the like Substituted heterocycle groups include the above-described heterocycle groups which are substituted one or more times by, for example, halogen, amino, alkyl, hydroxy, carboxy, and combinations thereof. Heterocycle groups may also be substituted by, e.g., aryl or heteroaryl.

The term "heterocyclealkyl" refers to a -(alkylene)-heterocycle group wherein the heterocycle and alkylene portions are in accordance with the previous discussions.

The term "aroyl" means an aryl-C(O)—, in which the aryl group is as previously described. Suitable aroyl groups include, but are not limited to, benzoyl and 1-naphthoyl.

The term "acyl" means an HC(O)—, alkyl-C(O)—, cycloalkyl-C(O)—, aryl-C(O)—, or heteroalkyl-C(O)—, in which the various groups are as previously described, e.g., acetyl, propionyl, benzoyl, pyridinylcarbonyl, and the like.

The term "alkoxy" means alkyl-O— groups in which the alkyl portion is in accordance with the previous discussion. Suitable alkoxy groups include, but are not limited to, methoxy, ethoxy, n-propoxy, iso-propoxy, n-butoxy, t-butoxy, pentoxy, hexoxy, heptoxy, octoxy, and the like. For example, the alkoxy can be methoxy or ethoxy.

The term "alkenyloxy" means alkenyl-O— groups in which the alkenyl portion is in accordance with the previous discussion. Suitable alkoxy groups include, but are not limited to, —OCH$_2$CH═CH$_2$.

The term "aryloxy" means an aryl-O— group, in which the aryl group is as previously described.

The term "heteroaryloxy" means an heteroaryl-O— group, in which the heteroaryl group is as previously described.

The term "cycloalkylalkyloxy" means a —O-(alkylene)-cycloalkyl group, in which the cycloalkyl and alkylene groups are as previously described.

The term "alkylthio" means an alkyl-S— group, in which the alkyl group is as previously described.

The term "arylthio" means an aryl-S— group, in which the aryl group is as previously described.

The term "alkylsulfinyl" means a —SOR radical where R is alkyl as defined above, e.g., methylsulfinyl, ethylsulfinyl, and the like.

The term "alkylsulfonyl" means a —SO$_2$R radical where R is alkyl as defined above, e.g., methylsulfonyl, ethylsulfonyl, and the like.

The term "arylsulfinyl" means a —SOR radical where R is aryl as defined above, e.g., phenylsulfinyl, and the like.

The term "arylsulfonyl" means a —SO$_2$R radical where R is aryl as defined above, e.g., phenylsulfonyl, and the like.

The term "heteroarylsulfinyl" means a —SOR radical where R is heteroaryl as defined above.

The term "heteroarylsulfonyl" means a —SO$_2$R radical where R is heteroaryl as defined above.

The term "alkoxycarbonyl" means an alkyl-O—C(O)— group, in which the alkyl group is as previously described.

The term "aryloxycarbonyl" means an aryl-O—C(O)— group, in which the aryl group is as previously described.

The term "heteroaryloxycarbonyl" means an heteroaryl-O—C(O)— group, in which the heteroaryl group is as previously described.

The term "cycloalkyloxy" means a —O-cycloalkyl group in which the cycloalkyl group is as previously described, e.g., cyclopropyloxy, cyclobutyloxy, cyclopentyloxy, cyclohexyloxy, and the like The term "arylalkyloxy" means —O-(alkylene)-aryl group, in which the aryl and alkylene groups are as previously described.

The term "heteroarylalkyloxy" means —O-(alkylene)-heteroaryl group, in which the heteroaryl and alkylene groups are as previously described.

One of ordinary skill in the art will recognize that compounds of formulas I and II can exist in different tautomeric and geometrical isomeric forms. All of these compounds, including cis isomers, trans isomers, diastereomic mixtures, racemates, nonracemic mixtures of enantiomers, substantially pure, and pure enantiomers, are within the scope of the present invention. Substantially pure enantiomers contain no more than 5% w/w of the corresponding opposite enantiomer, preferably no more than 2%, most preferably no more than 1%.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, dibenzoyltartaric, ditoluoyltartaric and camphorsulfonic acid. Mixtures of diastereoisomers can be separated into their individual diastereomers on the basis of their physical and/or chemical differences by methods known to those skilled in the art, for example, by chromatography or fractional crystallization. The optically active bases or acids are then liberated from the separated diastereomeric salts. A different process for separation of optical isomers involves the use of chiral chromatography (e.g., chiral HPLC columns), with or without conventional derivation, optimally chosen to maximize the separation of the enantiomers. Suitable chiral HPLC columns are manufactured by Diacel, e.g., Chiracel OD and Chiracel OJ among many others, all routinely selectable. Enzymatic separations, with or without derivitization, are also useful. The optically active compounds of formula I can likewise be obtained by utilizing optically active starting materials in chiral synthesis processes under reaction conditions which do not cause racemization.

In addition, one of ordinary skill in the art will recognize that the compounds can be used in different enriched isotopic forms, e.g., enriched in the content of $^2$H, $^3$H, $^{11}$C, $^{13}$C and/or $^{14}$C. In one particular embodiment, the compounds are deuterated. Such deuterated forms can be made the procedure described in U.S. Pat. Nos. 5,846,514 and 6,334,997. As described in U.S. Pat. Nos. 5,846,514 and 6,334,997, deuteration can improve the efficacy and increase the duration of action of drugs.

Deuterium substituted compounds can be synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] (2000), 110 pp. CAN 133:68895 AN 2000:473538 CAPLUS; Kabalka, George W.; Varma, Rajender S. The synthesis of radiolabeled compounds via organometallic intermediates. Tetrahedron (1989), 45(21), 6601-21, CODEN: TETRAB ISSN:0040-4020. CAN 112:20527 AN 1990:20527 CAPLUS; and Evans, E. Anthony. Synthesis of radiolabeled compounds, J. Radioanal. Chem. (1981), 64(1-2), 9-32. CODEN: JRACBN ISSN:0022-4081, CAN 95:76229 AN 1981:476229 CAPLUS.

Where applicable, the present invention also relates to useful forms of the compounds as disclosed herein, such as base free forms, and pharmaceutically acceptable salts or prodrugs of all the compounds of the present invention for which salts or prodrugs can be prepared. Pharmaceutically acceptable salts include those obtained by reacting the main compound, functioning as a base with an inorganic or organic acid to form a salt, for example, salts of hydrochloric acid, sulfuric acid, phosphoric acid, methane sulfonic acid, camphor sulfonic acid, oxalic acid, maleic acid, succinic acid, citric acid, formic acid, hydrobromic acid, benzoic acid, tartaric acid, fumaric acid, salicylic acid, mandelic acid, and carbonic acid. Pharmaceutically acceptable salts also include those in which the main compound functions as an acid and is reacted with an appropriate base to form, e.g., sodium, potassium, calcium, magnesium, ammonium, and choline salts. Those skilled in the art will further recognize that acid addition salts of the claimed compounds may be prepared by reaction of the compounds with the appropriate inorganic or organic acid via any of a number of known methods. Alternatively, alkali and alkaline earth metal salts can be prepared by reacting the compounds of the invention with the appropriate base via a variety of known methods.

The following are further examples of acid salts that can be obtained by reaction with inorganic or organic acids: acetates, adipates, alginates, citrates, aspartates, benzoates, benzenesulfonates, bisulfates, butyrates, camphorates, digluconates, cyclopentanepropionates, dodecylsulfates, ethanesulfonates, glucoheptanoates, glycerophosphates, hemisulfates, heptanoates, hexanoates, fumarates, hydrobromides, hydroiodides, 2-hydroxy-ethanesulfonates, lactates, maleates, methanesulfonates, nicotinates, 2-naphthalenesulfonates, oxalates, palmoates, pectinates, persulfates, 3-phenylpropionates, picrates, pivalates, propionates, succinates, tartrates, thiocyanates, tosylates, mesylates and undecanoates.

For example, the pharmaceutically acceptable salt can be a hydrochloride, a hydrobromide, a hydroformate, or a maleate.

Preferably, the salts formed are pharmaceutically acceptable for administration to mammals. However, pharmaceutically unacceptable salts of the compounds are suitable as intermediates, for example, for isolating the compound as a salt and then converting the salt back to the free base compound by treatment with an alkaline reagent. The free base can then, if desired, be converted to a pharmaceutically acceptable acid addition salt.

One of ordinary skill in the art will also recognize that some of the compounds of formulas I and II can exist in different polymorphic forms. As known in the art, polymorphism is an ability of a compound to crystallize as more than one distinct crystalline or "polymorphic" species. A polymorph is a solid crystalline phase of a compound with at least two different arrangements or polymorphic forms of that compound molecule in the solid state. Polymorphic forms of any given compound are defined by the same chemical formula or composition and are as distinct in chemical structure as crystalline structures of two different chemical compounds.

One of ordinary skill in the art will further recognize that compounds of formulas I and II can exist in different solvate forms. Solvates of the compounds of the invention may also form when solvent molecules are incorporated into the crystalline lattice structure of the compound molecule during the crystallization process.

The present invention also includes prodrugs of compounds of formulas I and II. The term prodrug is intended to represent covalently bonded carriers, which are capable of releasing the active ingredient of formulas I and II when the prodrug is administered to a mammalian subject. Release of the active ingredient occurs in vivo. Prodrugs can be prepared by techniques known to one skilled in the art. These techniques generally modify appropriate functional groups in a given compound. These modified functional groups however regenerate original functional groups by routine manipulation or in vivo. Prodrugs of compounds of formula I include compounds wherein a hydroxy, amino, carboxylic or a similar group is modified. Examples of prodrugs include, but are not limited to esters (e.g., acetate, formate, and benzoate derivatives), carbamates (e.g., N,N-dimethylaminocarbonyl) of hydroxy or amino functional groups in compounds of formula I), amides (e.g., trifluoroacetylamino, acetylamino, and the like), and the like. Prodrugs of compounds of formulas I and II are also within the scope of this invention.

The present invention also provides processes for preparing the compounds of formulas I and II. For example, the compounds may be prepared using the general reaction scheme outlined below.

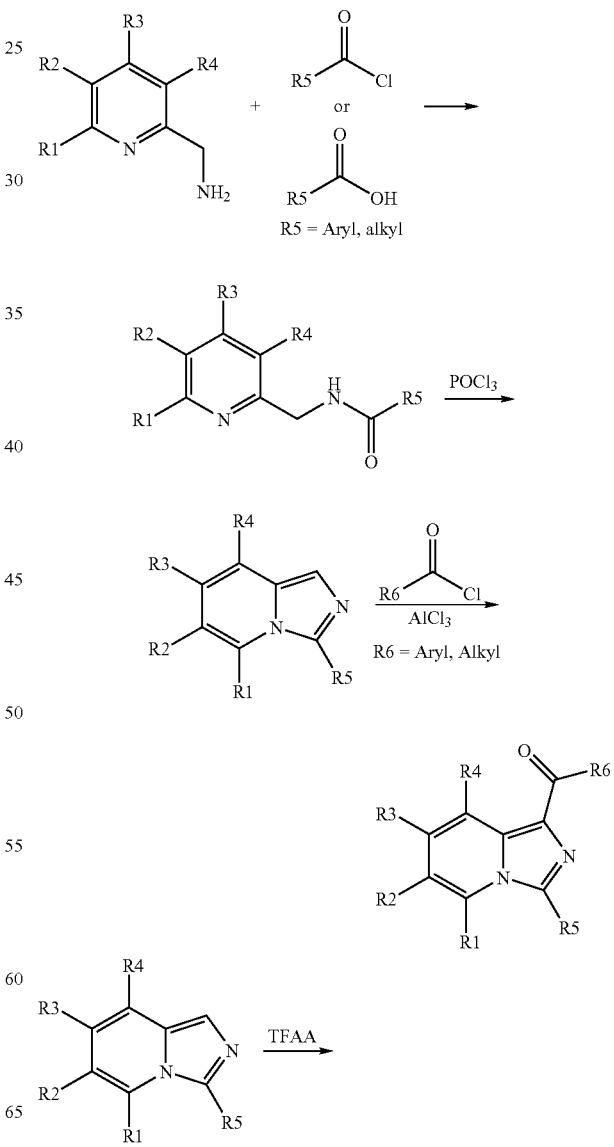

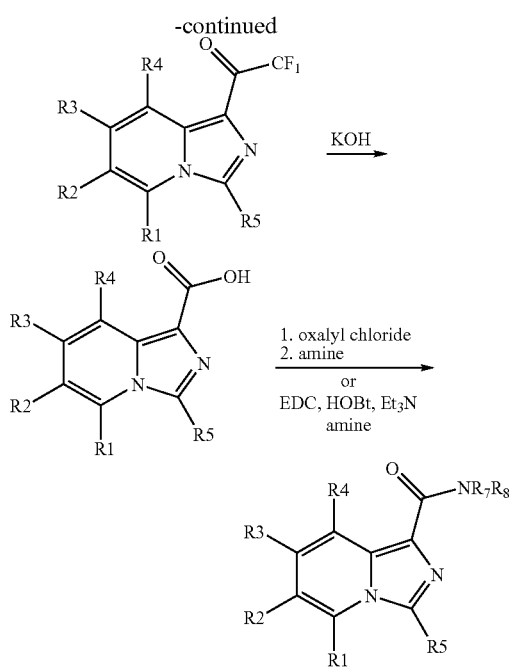

In the general reaction scheme, a 2-(aminomethyl)pyridine is acylated with an appropriate acid chloride or carboxylic acid under general coupling conditions. Subsequent cyclization/dehydration with POCl$_3$ affords the desired imidazopyrdine. Friedel-Crafts acylation produces the desired imidazopyrdine ketones. Hydrolysis of the trifluoromethyl ketone with potassium hydroxide provides the desired carboxylic acid, which is subsequently converted to the imidazopyridine amide. A variety of 2-(aminomethyl)pyridine compounds are commercially available (e.g., Aldrich, St. Louis, Mo.).

Numerous standard references are available that describe procedures for preparing various formulations suitable for administering the compounds according to the invention. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), 1553-1593 (current edition).

Administration of the compounds of the present invention may be accomplished according to patient needs, for example, orally, nasally, parenterally (subcutaneously, intraveneously, intramuscularly, intrasternally and by infusion) by inhalation, rectally, vaginally, topically and by ocular administration.

Various solid oral dosage forms can be used for administering compounds of the invention including such solid forms as tablets, gelcaps, capsules, caplets, granules, lozenges and bulk powders. The compounds of the present invention can be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms can also be used for administering compounds of the inventions, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the present invention can be prepared by mixing the compound with a suitable excipient such as cocoa butter, salicylates and polyethylene glycols. Formulations for vaginal administration can be in the form of a pessary, tampon, cream, gel, past foam, or spray formula containing, in addition to the active ingredient, such suitable carriers as are known in the art.

For topical administration the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

Aerosol formulations suitable for administering via inhalation also can be made. For example, the compounds according to the invention can be administered by inhalation in the form of a powder (e.g., micronized) or in the form of atomized solutions or suspensions. The aerosol formulation can be placed into a pressurized acceptable propellant.

The compounds of the present invention may be useful as cannabinoid receptor ligands. In exemplary embodiments, the compounds of the present invention may be useful as CB1 and/or CB2 receptor ligands. In preferred embodiments, the present invention the compounds of the present invention may possess preferentially high affinity for a CB2 receptor. Thus, the compounds of the present invention may be useful in the treatment of conditions that respond to cannabinoid receptor (e.g., CB2 receptor) agonists, inverse agonists and/or antagonists.

In some embodiments, the present invention provides methods for treating a condition that responds to a cannabinoid receptor (e.g., CB2 receptor) ligand. For example, some embodiments provide methods of treating a condition that responds to a cannabinoid receptor (e.g., CB2 receptor) agonist, an inverse agonist, or an antagonist comprising administering to a patient in need thereof an effective amount of a compound of the present invention.

In view of their ability to bind to the cannabinoid (e.g., CB2) receptor, the compounds of the invention may be useful in the treatment of the disorders that follow. Thus, the compounds of formula (I) may be useful as analgesics. For example they may be useful in the treatment of chronic inflammatory pain (e.g. pain associated with rheumatoid arthritis, osteo-arthritis, rheumatoid spondylitis, gouty arthritis and juvenile arthritis) including the property of disease modification and joint structure preservation; musculoskeletal pain; lower back and neck pain; sprains and strains; neuropathic pain; sympathetically maintained pain; myositis; pain associated with cancer and fibromyalgia; pain associated with migraine; pain associated with influenza or other viral infections, such as the common cold; rheumatic fever; pain associated with functional bowel disorders such as non-ulcer dyspepsia, non-cardiac chest pain and irritable bowel syndrome; pain associated with myocardial ischemia; post operative pain; headache; toothache; and dysmenorrhea.

The compounds of the invention may also be useful disease modification or joint structure preservation in multiple sclerosis, rheumatoid arthritis, osteo-arthritis, rheumatoid spondylitis, gouty arthritis and juvenile arthritis.

The compounds of the invention may be useful in the treatment of neuropathic pain. Neuropathic pain syndromes can develop following neuronal injury and the resulting pain may persist for months or years, even after the original injury has healed. Neuronal injury may occur in the peripheral nerves, dorsal roots, spinal cord or certain regions in the brain. Neuropathic pain syndromes are traditionally classified according to the disease or event that precipitated them. Neuropathic pain syndromes include: diabetic neuropathy; sciatica; non-specific lower back pain; multiple sclerosis pain; fibromyalgia; HIV-related neuropathy; post-herpetic neuralgia; trigeminal neuralgia; and pain resulting from physical trauma, amputation, cancer, toxins or chronic inflammatory conditions. These conditions are difficult to treat and although several drugs are known to have limited efficacy, complete pain control is rarely achieved. The symptoms of neuropathic pain are incredibly heterogeneous and are often described as spontaneous shooting and lancinating pain, or ongoing, burning pain. In addition, there is pain associated with normally non-painful sensations such as "pins and needles" (paraesthesias and dysesthesias), increased sensitivity to touch (hyperesthesia), painful sensation following innocuous stimulation (dynamic, static or thermal allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

The compounds of formulas I and II may also be useful in the treatment of fever.

The compounds of formulas I and II may also be useful in the treatment of inflammation, for example in the treatment of skin conditions (e.g. sunburn, burns, eczema, dermatitis, psoriasis); ophthalmic diseases such as glaucoma, retinitis, retinopathies, uveitis and of acute injury to the eye tissue (e.g. conjunctivitis); lung disorders (e.g. asthma, bronchitis, emphysema, allergic rhinitis, respiratory distress syndrome, pigeon fancier's disease, farmer's lung, chronic obstructive pulmonary disease, (COPD); gastrointestinal tract disorders (e.g. aphthous ulcer, Crohn's disease, atopic gastritis, gastritis varialoforme, ulcerative colitis, coeliac disease, regional ileitis, irritable bowel syndrome, inflammatory bowel disease, gastro esophageal reflux disease); organ transplantation; other conditions with an inflammatory component such as vascular disease, migraine, periarteritis nodosa, thyroiditis, aplastic anaemia, Hodgkin's disease, sclerodoma, myaesthenia gravis, multiple sclerosis, sorcoidosis, nephrotic syndrome, Bechet's syndrome, polymyositis, gingivitis, myocardial ischemia, pyrexia, systemic lupus erythematosus, tendinitis, bursitis, and Sjogren's syndrome.

The compounds of formulas I and II are also useful in the treatment of immunological diseases such as autoimmune diseases, immunological deficiency diseases or organ transplantation. The compounds of formulas I and II are also effective in increasing the latency of HIV infection.

The compounds of formulas I and II are also useful in the treatment of diseases of abnormal platelet function (e.g. occlusive vascular diseases).

The compounds of formulas I and II are also useful in the treatment of neurodegenerative diseases and neurodegeneration such as dementia, particularly degenerative dementia (including senile dementia, Alzheimer's disease, Pick's disease, Huntingdon's chorea, Parkinson's disease and Creutzfeldt-Jakob disease, motor neuron disease); vascular dementia (including multi-infarct dementia); as well as dementia associated with intracranial space occupying lesions; trauma; infections and related conditions (including HIV infection); dementia in Parkinson's disease; metabolism; toxins; anoxia and vitamin deficiency; and mild cognitive impairment associated with ageing, particularly Age Associated Memory Impairment. The compounds may also be useful for the treatment of amyotrophic lateral sclerosis (ALS) and neuroinflamation.

The compounds of formulas I and II are also useful in neuroprotection and in the treatment of neurodegeneration following stroke, cardiac arrest, pulmonary bypass, traumatic brain injury, spinal cord injury or the like.

The compounds of formulas I and II are also useful in the treatment of tinnitus.

The compounds of formulas I and II are also useful in the treatment of psychiatric disease for example schizophrenia, depression (which term is used herein to include bipolar depression, unipolar depression, single or recurrent major depressive episodes with or without psychotic features, catatonic features, melancholic features, atypical features or post-partum onset, seasonal affective disorder, dysthymic disorders with early or late onset and with or without atypical features, neurotic depression and social phobia, depression accompanying dementia for example of the Alzheimer's type, schizoaffective disorder or the depressed type, and depressive disorders resulting from general medical conditions including, but not limited to, myocardial infarction, diabetes, miscarriage or abortion, etc), anxiety disorders (including generalised anxiety disorder and social anxiety disorder), panic disorder, agoraphobia, social phobia, obsessive compulsive disorder and post-traumatic stress disorder, memory disorders, including dementia, amnesic disorders and age-associated memory impairment, disorders of eating behaviours, including anorexia nervosa and bulimia nervosa, sexual dysfunction, sleep disorders (including disturbances of circadian rhythm, dyssomnia, insomnia, sleep apnea and narcolepsy), withdrawal from abuse of drugs such as of cocaine, ethanol, nicotine, benzodiazepines, alcohol, caffeine, phencyclidine (phencyclidine-like compounds), opiates (e.g. cannabis, heroin, morphine), amphetamine or amphetamine-related drugs (e.g. dextroamphetamine, methylamphetamine) or a combination thereof.

The compounds of formulas I and II are also useful in preventing or reducing dependence on, or preventing or reducing tolerance or reverse tolerance to, a dependence-inducing agent. Examples of dependence inducing agents include opioids (e.g. morphine), CNS depressants (e.g. ethanol), psychostimulants (e.g. cocaine) and nicotine.

The compounds of formulas I and II are also useful in the treatment of kidney dysfunction (nephritis, particularly mesangial proliferative glomerulonephritis, nephritic syndrome), liver dysfunction (hepatitis, cirrhosis), gastrointestinal dysfunction (diarrhoea) and colon cancer.

The compounds of formulas I and II may be useful to target and kill tumors, e.g., tumors of immune origin, are thus may also be useful in the treatment of cancers of immune origin e.g., malignant lymphoblastic disease. See, e.g., Blood, 100, (2), 627-634, 2002.

The term "treating" means to relieve, alleviate, delay, reduce, reverse, improve or prevent at least one symptom of a condition in a subject. The term "treating" may also mean to arrest, delay the onset (i.e., the period prior to clinical manifestation of a disease) and/or reduce the risk of developing or worsening a condition.

An "effective amount" means the amount of a compound of formula I that, when administered to a patient (e.g., a mammal) for treating a disease, is sufficient to effect such treatment for the disease to achieve the objectives of the invention. The "effective amount" will vary depending on the compound, the disease and its severity and the age, weight, etc., of the patient to be treated.

A subject or patient in whom administration of the therapeutic compound is an effective therapeutic regimen for a disease or disorder is preferably a human, but can be any animal, including a laboratory animal in the context of a clinical trial or screening or activity experiment. Thus, as can be readily appreciated by one of ordinary skill in the art, the methods, compounds and compositions of the present invention are particularly suited to administration to any animal, particularly a mammal, and including, but by no means limited to, humans, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

In some embodiments, the compounds of the present invention are administered as a mono-therapy. In other embodiments, the compounds of the present invention are administered as part of a combination therapy. For example, a compound of formula I may be used in combination with other drugs or therapies that are used in the treatment/prevention/suppression or amelioration of the diseases or conditions for which compounds of formula I are useful.

Such other drug(s) may be administered, by a route and in an amount commonly used therefor, contemporaneously or sequentially with a compound of formula I and/or II. When a compound of formula I and/or II is used contemporaneously with one or more other drugs, a pharmaceutical unit dosage form containing such other drugs in addition to the compound of formula I may be employed. Accordingly, the pharmaceutical compositions of the present invention include those that also contain one or more other active ingredients, in addition to a compound of formulas I and/or II.

EXAMPLES

The present invention will now be further described by way of the following non-limiting examples. In applying the disclosure of these examples, it should be kept clearly in mind that other and different embodiments of the methods and schemes disclosed herein will no doubt suggest themselves to those of ordinary skill in the relevant art.

Example 1

Preparation of 1-(3-naphthalen-1-yl-imidazo[1,5-a]pyridin-1-yl)-butan-1-one

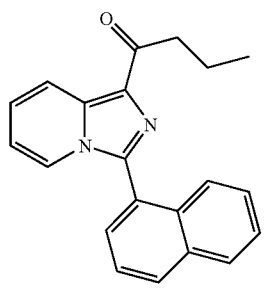

To a solution of 2-(aminomethyl)pyridine (1.4 mL, 13.9 mmol) in dichloromethane (50 mL) was added naphtholyl-chloride (1.9 mL) slowly over 5 min. The mixture was allowed to stir at ambient temperature for 30 min. then washed with water. The organic layer was dried over anhydrous sodium sulfate and concentrated in vacuo to yield naphthalene-1-carboxylic acid (pyridin-2-ylmethyl)-amide (2.90 g, 88% yield). This material was used without further purification.

To a solution of naphthalene-1-carboxylic acid (pyridin-2-ylmethyl)-amide (2.80 g, 10.7 mmol) in toluene (100 mL) was added POCl$_3$ (9 mL). The mixture was heated to 90° C. for 12 h. After this time the mixture was allowed to cool and poured slowly into 10% aqueous potassium carbonate (500 mL). The mixture was extracted with ethyl acetate (2×100 mL) and the combined organic layers were dried over anhydrous sodium sulfate and concentrated in vacuo. The residue was chromatographed on silica to yield 3-naphthalen-1-yl-imidazo[1,5-a]pyridine (1.89 g, 72%).

To a solution of butyroylchloride (100 μL, 1.13 mmol) in dichloromethane (10 mL) was added aluminum trichloride (195 mg, 1.47 mmol). The mixture was allowed to stir for 10 min. then a solution of 3-naphthalen-1-yl-imidazo[1,5-a]pyridine (276 mg, 1.13 mmol) in dichloromethane (5 mL) was added. The mixture was stirred for 30 min. at ambient temperature then washed with saturated aqueous sodium bicarbonate and the organic layer was dried over anhydrous sodium sulfate and concentrated in vacuo. The residue was chromatographed on silica to yield the title compound (25 mg, 8%). $^1$H NMR (DMSO-$_{d6}$) δ 8.27 (1H), 8.19 (1H), 8.10 (1H), 7.95 (1H), 7.85 (1H), 7.68 (1H), 7.60 (2H), 7.55 (1H), 7.40 (1H), 6.95 (1H), 3.04 (2H), 1.70 (2H), 0.90 (3H); m/z (M+H)=315.2.

Example 2

Preparation of (2-iodo-phenyl)-(3-naphthalen-1-yl-imidazo[1,5-a]pyridin-1-yl)-methanone

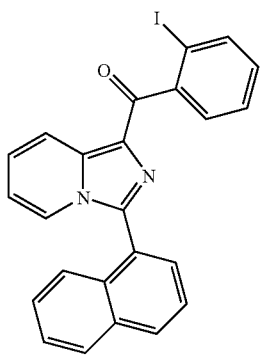

To a solution of 2-iodobenzoic acid (487 mg, 1.83 mmol) in 1,2-dichloroethane (20 mL) was added aluminum trichloride (266 mg, 2.00 mmol). The mixture was allowed to stir for 10 min. then a solution of 3-naphthalen-1-yl-imidazo[1,5-a]pyridine (212 mg, 0.87 mmol) in 1,2-dichloroethane (5 mL) was added. The mixture was stirred at ambient temperature for 30 min. then washed with saturated aqueous sodium bicarbonate and the organic layer was dried over anhydrous sodium sulfate and concentrated in vacuo. The residue was chromatographed on silica to yield the title compound (76 mg, 18%). 8.37 (1H), 8.18 (1H), 8.10 (2H), 7.92 (1H), 7.85 (1H), 7.71 (2H), 7.56 (5H), 7.20 (1H), 7.07 (1H); m/z (M+H)=475.1.

Example 3

Preparation of 2,2,2-trifluoro-1-(3-naphthalen-1-yl-imidazo[1,5-a]pyridin-1-yl)-ethanone

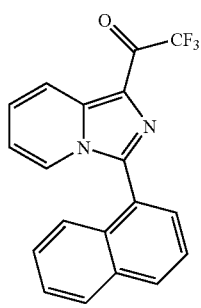

A solution of 3-naphthalen-1-yl-imidazo[1,5-a]pyridine (300 mg, 1.23 mmol) in DMF (10 mL) was cooled in an ice bath. To this mixture was added trifluoroacetic anhydride (0.22 mL, 1.60 mmol). The mixture was allowed to stir for 30 min. After this time an additional portion of trifluoroacetic anhydride (0.22 mL) was added and the mixture was stirred for an additional 30 min. After this time the mixture was poured into water (100 mL) and stirred for 30 min. The resulting precipitate was filtered and dried to yield the title compound (326 mg, 78%). $^1$H NMR (DMSO-$d_6$) δ 8.41 (1H), 8.25 (2H), 8.12 (1H), 7.93 (1H), 7.76 (2H), 7.70 (1H), 7.64 (1H), 7.56 (1H), 7.21 (1H); m/z (M+H)=341.2.

Example 4

Preparation of 3-naphthalen-1-yl-imidazo[1,5-a]pyridine-1-carboxylic acid

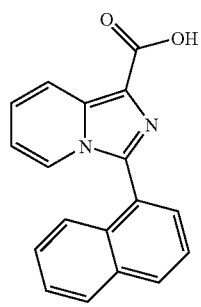

To a solution of 2,2,2-trifluoro-1-(3-naphthalen-1-yl-imidazo[1,5-a]pyridin-1-yl)-ethanone (260 mg, 0.76 mmol) in EtOH (10 mL) was added KOH (582 mg, 10.4 mmol) and the mixture was heated to reflux for 30 min. The mixture was allowed to cool and concentrated. The residue was dissolved in water (25 mL) and acidified to pH 3 with 2N HCl. The precipitate was filtered, dried and recrystallized from ethyl acetate to yield the title compound (120 mg, 55%). 8.30 (1H), 8.10 (2H), 7.78 (2H), 7.70 (1H), 7.59 (2H), 7.52 (1H), 7.02 (1H), 6.70 (1H); m/z (M+H)=289.24.

Example 5

Preparation of 3-naphthalen-1-yl-imidazo[1,5-a]pyridine-1-carboxylic acid adamantan-1-ylamide

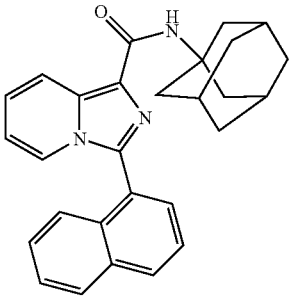

To a solution of 3-naphthalen-1-yl-imidazo[1,5-a]pyridine-1-carboxylic acid (55 mg, 0.19 mmol) in DMF (5 mL) was added EDC (161 mg, 0.84 mmol), HOBt, (90 mg, 0.67 mmol) and Et$_3$N (0.23 mL, 1.68 mmol). The mixture was allowed to stir for 10 min. and adamantylamine (93 mg, 0.62 mmol) was added. The mixture was stirred for 15 h then diluted with ethyl acetate (30 mL) and washed with water (50 mL). The organic layer was dried over anhydrous sodium sulfate and concentrated in vacuo. The residue was chromatographed on silica to yield the title compound (67 mg, 84%).

Example 6

Preparation of 3-butyl-imidazo[1,5-a]pyridin-1-yl-naphthalen-1-yl-methanone

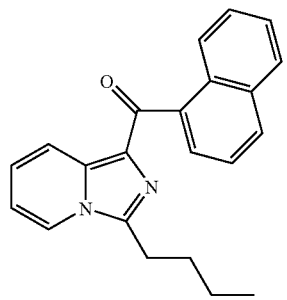

To a solution of pentanoic acid (5.3 mL, 48.7 mmol) in THF (50 mL) was added EDC (11.2 g, 58.4 mmol) and HOBt (7.88 g, 58.4 mmol). The mixture was stirred for 10 min. then 2-(aminomethyl)pyridine (4.7 mL, 46.3 mmol) was added. The solution was allowed to stir for 3 h then quenched with water (100 mL). The mixture was extracted with ethyl acetate (2×100 mL) and the combined organic layers were dried over anhydrous sodium sulfate and concentrated in vacuo to yield pentanoic acid (pyridin-2-ylmethyl)-amide (8.60, 92%).

To a solution of pentanoic acid (pyridin-2-ylmethyl)-amide (7.5 g, 39.1 mmol) in 1,2-dichloroethane (100 mL), cooled in an ice bath, was added POCl$_3$ (12 mL). The mixture was heated to 80° C. for 4 h. After this time the mixture was allowed to cool and poured slowly into 10% aqueous potassium carbonate (500 mL). The mixture was extracted with dichloromethane (2×200 mL) and the combined organic layers were dried over anhydrous sodium sulfate and concentrated in vacuo. The residue was chromatographed on silica to yield the 4-butyl-imidazo[1,5-a]pyridine (3.42, 50%)

To a solution of 1-naphthoyl chloride (0.350 ml, 2.31 mmol, 2 eq) in 1,2-dichloroethane (8 ml) was added aluminum trichloride (354 mg, 2.65 mmol, 2.3 eq). The reaction mixture was stirred at room temperature for 10 min., then a solution of 4-butyl-imidazo[1,5-a]pyridine (201 mg, 1.15 mmol) in 1,2-dichloroethane (5 ml) was added. The reaction mixture was stirred at room temperature for 1 hour. Then washed with saturated aqueous sodium bicarbonate and the organic layer was dried over anhydrous sodium sulfate and concentrated in vacuo. The residue was chromatographed on silica to yield the title compound (124 mg, 32.9%). $^1$H NMR (DMSO-$_{d6}$) δ 8.57 (1H), 8.29 (1H), 8.09-8.01 (3H), 7.78 (1H), 7.67 (1H), 7.57 (1H), 7.45 (1H), 7.43 (1H), 7.12 (1H), 3.01 (2H), 1.56 (2H), 1.34 (2H), 0.09 (3H); m/z (M+H)= 329.19.

Example 7

Preparation of (3-butyl-imidazo[1,5-a]pyridin-1-yl)-(2-iodo-phenyl)-methanone

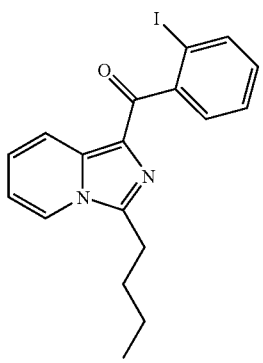

To a solution of 2-iodobenzoic acid (487 mg, 1.83 mmol) in 1,2-dichloroethane (20 mL) was added aluminum trichloride (266 mg, 2.00 mmol). The mixture was allowed to stir for 10 min. then a solution of 4-butyl-imidazo[1,5-a]pyridine (151 mg, 0.87 mmol) in 1,2-dichloroethane (5 mL) was added. The mixture was stirred at ambient temperature for 30 min. then washed with saturated aqueous sodium bicarbonate and the organic layer was dried over anhydrous sodium sulfate and concentrated in vacuo. The residue was chromatographed on silica to yield the title compound (67 mg, 19%). $^1$H NMR (DMSO-$_{d6}$) δ 8.53 (1H), 8.11 (1H), 7.92 (1H), 7.49 (1H), 7.41 (2H), 7.24 (1H), 7.10 (1H), 3.00 (2H), 1.67 (2H), 1.37 (2H), 0.90 (3H); m/z (M+H)=405.1.

Example 8

Preparation of 3-butyl-imidazo[1,5-a]pyridin-1-yl)-2-(2-iodo-5-nitro-phenyl)-methanone

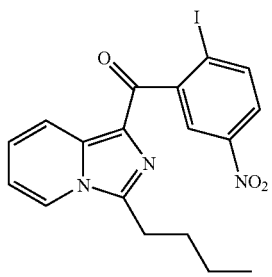

To a solution of 2-iodo-5-nitro-benzoyl chloride in DCM (2 ml) was added aluminum trichloride (154 mg, 1.15 mmol, 2.0 eq). The reaction mixture was stirred at room temperature for 10 min., then a solution of 4-butyl-imidazo[1,5-a]pyridine (95 mg, 0.546 mmol) in DCM (1 ml) was added. The reaction mixture was stirred at room temperature for 1 hour. Then washed with saturated aqueous sodium bicarbonate and the organic layer was dried over anhydrous sodium sulfate and concentrated in vacuo. The residue was chromatographed on silica to yield the title compound (56 mg, 23%). $^1$H NMR (DMSO-$_{d6}$) δ 8.60 (1H), 8.24 (3H), 8.10 (1H), 7.5 (1H), 7.18 (1H), 3.01 (2H), 1.64 (2H), 1.38 (2H), 0.09 (3H); m/z (M+H)= 450.1

Example 9

Preparation of 1-(3-butyl-imidazo[1,5-a]pyridin-1-yl)-2,2,2-trifluoro-ethanone

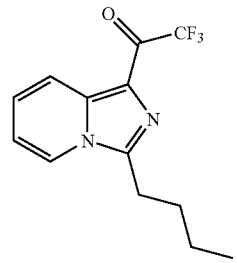

A solution of 4-butyl-imidazo[1,5-a]pyridine (500 mg, 2.87 mmol) in DMF (10 mL) was cooled in an ice bath. To this mixture was added trifluoroacetic anhydride (0.88 mL, 6.32 mmol). The mixture was allowed to stir for 3 h. After this time the mixture was poured into 10% potassium carbonate (100 mL) and stirred for 1 h. The resulting precipitate was filtered and dried to yield the title compound (624 mg, 81%). $^1$H NMR (DMSO-$_{d6}$) δ 8.72 (1H), 8.24 (1H), 7.66 (1H), 7.27 (1H), 3.10 (2H), 1.77 (2H), 1.42 (2H), 0.94 (3H); m/z (M+H)= 271.1.

Example 10

Preparation of 3-butyl-imidazo[1,5-a]pyridine-1-carboxylic acid

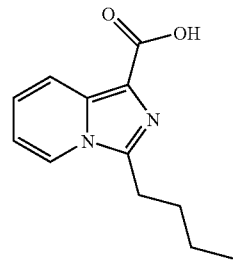

To a solution of 1-(3-butyl-imidazo[1,5-a]pyridin-1-yl)-2,2,2-trifluoro-ethanone (400 mg, 1.48 mmol) in EtOH (10 mL) was added KOH (830 mg, 14.8 mmol). The mixture was stirred at ambient temperature for 15 h. After this time the mixture was concentrated, diluted with water (10 mL) and acidified to pH 3 with 2N HCl. The aqueous mixture was extracted with ethyl acetate (3×50 mL) and the combined organic layers were dried over anhydrous sodium sulfate and concentrated in vacuo to yield the title compound (200 mg, 62%). $^1$H NMR (DMSO-$_{d6}$) δ 12.1 (1H), 8.38 (1H), 7.99 (1H), 7.18 (1H), 6.90 (1H), 2.99 (2H), 1.75 (2H), 1.38 (2H), 0.92 (3H); m/z (M+H)=219.0.

Example 11

Preparation of 3-butyl-imidazo[1,5-a]pyridine-1-carboxylic acid adamantan-1-ylamide

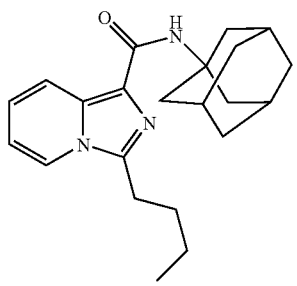

To a solution of 3-butyl-imidazo[1,5-a]pyridine-1-carboxylic acid (150 mg, 0.56 mmol) in DMF (5 mL) was added EDC (161 mg, 0.84 mmol), HOBt, (90 mg, 0.67 mmol) and Et$_3$N (0.23 mL, 1.68 mmol). The mixture was allowed to stir for 10 min. and adamantylamine (93 mg, 0.62 mmol) was added. The mixture was stirred for 15 h then diluted with ethyl acetate (30 mL) and washed with water (50 mL). The organic layer was dried over anhydrous sodium sulfate and concentrated in vacuo. The residue was chromatographed on silica to yield the title compound (157 mg, 80%). $^1$H NMR (DMSO-d$_6$) δ 8.31 (1H), 8.02 (1H), 7.04 (1H), 6.93 (1H), 6.81 (1H), 2.99 (2H), 2.08 (9H), 1.67 (8H), 1.38 (2H), 0.92 (3H); m/z (M+H)=352.1.

Example 12

Preparation of 3-propyl-imidazo[1,5-a]pyridin-1-yl-naphthalen-1-yl-methanone

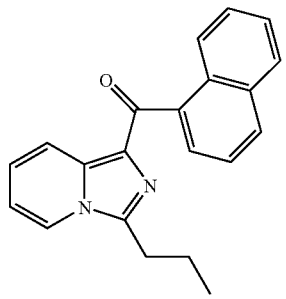

To a solution of butyric acid (4.5 mL, 48.7 mmol) in THF (50 mL) was added EDC (11.2 g, 58.4 mmol) and HOBt (7.88 g, 58.4 mmol). The mixture was stirred for 10 min. then 2-(aminomethyl)pyridine (4.7 mL, 46.3 mmol) was added. The solution was allowed to stir for 3 h then quenched with water (100 mL). The mixture was extracted with ethyl acetate (2×100 mL) and the combined organic layers were dried over anhydrous sodium sulfate and concentrated in vacuo to yield N-pyridin-2-ylmethyl-butyramide (5.82 g, 67%).

To a suspension of N-pyridin-2-ylmethyl-butyramide (5.5 g, 30.9 mmol) in toluene (100 mL), cooled in an ice bath, was added POCl$_3$ (12 mL). The mixture was heated to 90° C. for 5 h. After this time the mixture was allowed to cool and poured slowly into 10% aqueous potassium carbonate (500 mL). The mixture was extracted with ethyl acetate (2×200 mL) and the combined organic layers were dried over anhydrous sodium sulfate and concentrated in vacuo. The residue was chromatographed on silica to yield the title compound 3-propyl-imidazo[1,5-a]pyridine (4.94 g, 46%)

To a solution of 1-naphthoyl chloride (409 ml, 2.70 mmol, 2 eq) in 1,2-dichloroethane (10 ml) was added aluminum trichloride (415 mg, 3.11 mmol, 2.3 eq). The reaction mixture was stirred at room temperature for 10 min., then a solution of 3-propyl-imidazo[1,5-a]pyridine (216 mg, 1.35 mmol) in 1,2-dichloroethane (5 ml) was added. The reaction mixture was stirred at room temperature for 1 h. Then washed with saturated aqueous sodium bicarbonate and the organic layer was dried over anhydrous sodium sulfate and concentrated in vacuo. The residue was chromatographed on silica to yield the title compound (119 mg, 28%). $^1$H NMR (DMSO-$_{d6}$) δ 8.59 (1H), 8.28 (1H), 8.10-8.01 (3H), 7.80 (1H), 7.61 (1H), 7.57 (1H), 7.43 (1H), 7.41 (1H), 7.12 (1H), 2.92 (2H), 1.67 (2H), 0.09 (3H); m/z (M+H)=315.17.

Example 13

Preparation of (2-iodo-phenyl)-(3-propyl-imidazo[1,5-a]pyridin-1-yl)-methanone

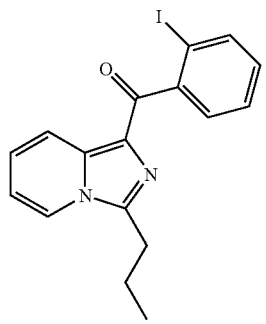

To a solution of 2-iodobenzoic acid (487 mg, 1.83 mmol) in 1,2-dichloroethane (20 mL) was added aluminum trichloride (266 mg, 2.00 mmol). The mixture was allowed to stir for 10 min. then a solution of 3-propyl-imidazo[1,5-a]pyridine (139 mg, 0.87 mmol) in 1,2-dichloroethane (5 mL) was added. The mixture was stirred at ambient temperature for 30 min. then washed with saturated aqueous sodium bicarbonate and the organic layer was dried over anhydrous sodium sulfate and concentrated in vacuo. The residue was chromatographed on silica to yield the title compound (50 mg, 15%). $^1$H NMR (DMSO-$_{d6}$) δ 8.54 (1H), 8.10 (1H), 7.92 (1H), 7.50 (1H), 7.41 (2H), 7.22 (1H), 7.10 (1H), 3.00 (2H), 1.70 (2H), 0.94 (3H); m/z (M+H)=391.1.

Example 14

Preparation of 2,2,2-trifluoro-1-(3-propyl-imidazo[1,5-a]pyridin-1-yl)-ethanone

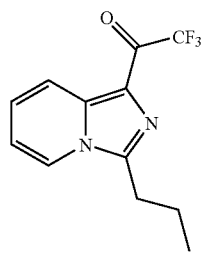

A solution of 3-propyl-imidazo[1,5-a]pyridine (459 mg, 2.87 mmol) in DMF (10 mL) was cooled in an ice bath. To this mixture was added trifluoroacetic anhydride (0.88 mL, 6.32 mmol). The mixture was allowed to stir for 3 h. After this time the mixture was poured into 10% potassium carbonate (100 mL) and stirred for 1 h. The resulting precipitate was filtered and dried to yield the title compound (575 mg, 78%). $^1$H NMR (DMSO-$_{d6}$) δ 8.70 (1H), 8.25 (1H), 7.66 (1H), 7.27 (1H), 3.06 (2H), 1.81 (2H), 1.01 (3H); m/z (M+H)=257.1.

Example 15

Preparation of 3-propyl-imidazo[1,5-a]pyridine-1-carboxylic acid

To a solution of 2,2,2-trifluoro-1-(3-propyl-imidazo[1,5-a]pyridin-1-yl)-ethanone (379 mg, 1.48 mmol) in EtOH (10 mL) was added KOH (830 mg, 14.8 mmol). The mixture was stirred at ambient temperature for 15 h. After this time the mixture was concentrated, diluted with water (10 mL) and acidified to pH 3 with 2N HCl. The aqueous mixture was extracted with ethyl acetate (3×50 mL) and the combined organic layers were dried over anhydrous sodium sulfate and concentrated in vacuo to yield the title compound (170 mg, 56%). $^1$H NMR (DMSO-$_{d6}$) δ 12.1 (1H), 8.38 (1H), 7.99 (1H), 7.18 (1H), 6.90 (1H), 2.99 (2H), 1.79 (2H), 0.98 (3H); m/z (M+H)=205.0.

Example 16

Preparation of 3-propyl-imidazo[1,5-a]pyridine-1-carboxylic acid adamantan-1-ylamide

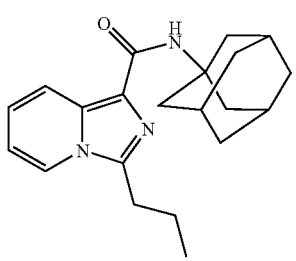

To a solution of 3-propyl-imidazo[1,5-a]pyridine-1-carboxylic acid (114 mg, 0.44 mmol) in DMF (5 mL) was added EDC (161 mg, 0.84 mmol), HOBt, (90 mg, 0.67 mmol) and Et$_3$N (0.23 mL, 1.68 mmol). The mixture was allowed to stir for 10 min. and adamantylamine (93 mg, 0.62 mmol) was added. The mixture was stirred for 15 h. then diluted with ethyl acetate (30 mL) and washed with water (50 mL). The organic layer was dried over anhydrous sodium sulfate and concentrated in vacuo. The residue was chromatographed on silica to yield the title compound (117 mg, 79%). $^1$H NMR (DMSO-$_{d6}$) δ 8.31 (1H), 8.02 (1H), 7.04 (1H), 6.93 (1H), 6.81 (1H), 2.97 (2H), 2.07 (9H), 1.76 (2H), 1.67 (6H), 0.96 (3H); m/z (M+H)=338.1.

Example 17

Preparation of [3-(2-morpholin-4-yl-ethyl)-imidazo[1,5-a]pyridin-1-yl]-naphthalen-1-yl-methanone

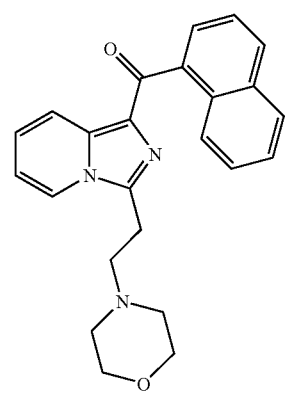

To a solution of methyl 4-morpholinepropionate (5.0 g, 28.9 mmol) in MeOH (25 mL) was added 2N NaOH (17.3 mL, 34.6 mmol). The mixture was stirred for 1 h then concentrated in vacuo. The residue was suspended in dichloromethane (125 mL) and DMF (30 μL) was added followed by oxalylchloride (10 mL, 115.6 mmol). The mixture was allowed to stir for 2 h. then concentrated in vacuo. The resulting solid was added portion-wise to a solution of 2-(aminomethyl)pyridine (2.88 mL, 28.2 mmol) and triethylamine (9.0 mL, 64.86 mmol) in dichloromethane (200 mL). The mixture was stirred at ambient temperature for 1 h. then washed with water (300 mL). The organic layer was dried over anhydrous sodium sulfate and concentrated to yield 3-morpholin-4-yl-N-pyridin-2-ylmethyl-propionamide (5.56 g, 77%).

To a solution of 3-morpholin-4-yl-N-pyridin-2-ylmethyl-propionamide (5.4 g, 21.7 mmol) in 1,2-dichloroethane (100 mL), cooled in an ice bath, was added $POCl_3$ (12 mL). The mixture was heated to 80° C. for 3 h. After this time the mixture was allowed to cool and poured slowly into 10% aqueous potassium carbonate (500 mL). The mixture was extracted with dichloromethane (200 mL) and ethyl acetate (200 mL) and the combined organic layers were dried over anhydrous sodium sulfate and concentrated in vacuo. The residue was chromatographed on silica to yield 3-(2-morpholin-4-yl-ethyl)-imidazo[1,5-a]pyridine (3.89, 78%).

To a solution of naphthoylchloride (0.28 mL, 1.85 mmol) in 1,2-dichloroethane (20 mL) was added aluminum trichloride (300 mg, 2.25 mmol). The mixture was allowed to stir for 10 min. then a solution of 3-(2-morpholin-4-yl-ethyl)-imidazo[1,5-a]pyridine (200 mg, 0.87 mmol) in 1,2-dichloroethane (5 mL) was added. The mixture was stirred at ambient temperature for 30 min. then washed with saturated aqueous sodium bicarbonate and the organic layer was dried over anhydrous sodium sulfate and concentrated in vacuo. The residue was chromatographed on silica to yield the title compound (160 mg, 48%). $^1$H NMR (DMSO-$d_6$) δ 8.56 (1H), 8.27 (1H), 8.07 (1H), 8.02 (2H), 7.76 (1H), 7.51 (4H), 7.11 (1H), 3.52 (4H), 3.18 (2H), 2.67 (2H), 2.40 (4H); m/z (M+H)=386.2.

Example 18

Preparation of (2-iodo-phenyl)-[3-(2-morpholin-4-yl-ethyl)-imidazo[1,5-a]pyridin-1-yl]-methanone

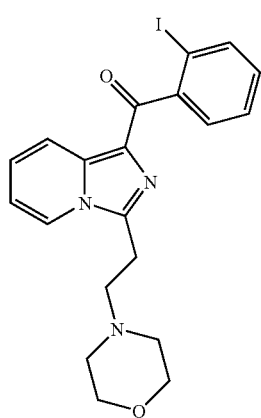

To a solution of 2-iodobenzoic acid (487 mg, 1.83 mmol) in 1,2-dichloroethane (20 mL) was added aluminum trichloride (266 mg, 2.00 mmol). The mixture was allowed to stir for 10 min. then a solution of 3-(2-morpholin-4-yl-ethyl)-imidazo[1,5-a]pyridine (201 mg, 0.87 mmol) in 1,2-dichloroethane (5 mL) was added. The mixture was stirred at ambient temperature for 30 min. then washed with saturated aqueous sodium bicarbonate and the organic layer was dried over anhydrous sodium sulfate and concentrated in vacuo. The residue was chromatographed on silica to yield the title compound (63 mg, 16%). %). $^1$H NMR (DMSO-d6) 8.54 (1H), 8.10 (1H), 7.92 (1H), 7.50 (1H), 7.41 (2H), 7.22 (1H), 7.10 (1H), 3.52 (4H), 3.18 (2H), 2.67 (2H), 2.40 (4H); m/z (M+H)=462.1.

Example 19

Preparation of 2,2,2-trifluoro-1-[3-(2-morpholin-4-yl-ethyl)-imidazo[1,5-a]pyridin-1-yl]-ethanone

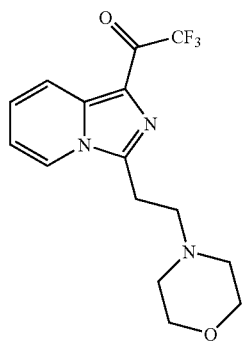

A solution of 3-(2-morpholin-4-yl-ethyl)-imidazo[1,5-a]pyridine (660 mg, 2.87 mmol) in DMF (10 mL) was cooled in an ice bath. To this mixture was added trifluoroacetic anhydride (0.88 mL, 6.32 mmol). The mixture was allowed to stir for 3 h. After this time the mixture was poured into 10% potassium carbonate (100 mL) and stirred for 1 h. The resulting precipitate was filtered and dried to yield the title compound (634 mg, 68%). $^1$H NMR (DMSO-$d_6$) δ 8.72 (1H), 8.24 (1H), 7.66 (1H), 7.27 (1H), 3.54 (4H), 3.28 (2H), 2.81 (2H), 2.47 (4H); m/z (M+H)=328.1.

Example 20

Preparation of 3-(2-morpholin-4-yl-ethyl)-imidazo[1,5-a]pyridine-1-carboxylic acid adamantan-1-ylamide

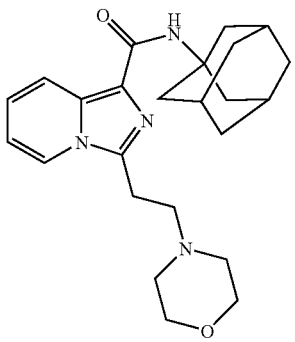

To a solution of 3-(2-morpholin-4-yl-ethyl)-imidazo[1,5-a]pyridine-1-carboxylic acid (150 mg, 0.54 mmol) in DMF (5 mL) was added EDC (161 mg, 0.84 mmol), HOBt, (90 mg, 0.67 mmol) and $Et_3N$ (0.23 mL, 1.68 mmol). The mixture was allowed to stir for 10 min. and adamantylamine (93 mg, 0.62 mmol) was added. The mixture was stirred for 15 h. then diluted with ethyl acetate (30 mL) and washed with water (50 mL). The organic layer was dried over anhydrous sodium sulfate and concentrated in vacuo. The residue was chromatographed on silica to yield the title compound (195 mg, 89%). ¹H NMR (DMSO-d6) δ 8.32 (1H), 8.02 (1H), 7.05 (1H), 6.93 (1H), 6.82 (1H), 3.56 (4H), 3.16 (2H), 2.73 (2H), 2.46 (4H), 2.07 (9H), 1.67 (6H); m/z (M+H)=409.18.

Example 21

Preparation of 3-(2-morpholin-4-yl-ethyl)-imidazo[1,5-a]pyridine-1-carboxylic acid piperidin-1-ylamide

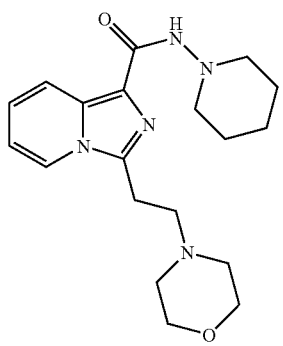

To a solution of 1-aminopiperidine (0.060 mL, 0.54 mmol) and triethylamine (0.16 mL, 1.14 mmol) in CH₂Cl₂ (10 mL) was added 3-(2-morpholin-4-yl-ethyl)-imidazo[1,5-a]pyridine-1-carbonyl chloride hydrochloride (150 mg, 0.45 mmol). The mixture was stirred at ambient temperature for 1 h. then washed with sat. aq. NaHCO₃ (20 mL). The organic layer was separated and the aqueous layer was extracted with dichloromethane (20 mL). The combined organic layers were dried over anhydrous sodium sulfate and concentrated in vacuo. The residue was chromatographed on silica to yield the title compound (55 mg, 34%). ¹H NMR (DMSO-$d_6$) δ 8.59 (1H), 8.35 (1H), 8.02 (1H), 7.08 (1H), 6.82 (1H), 3.57 (4H), 3.18 (2H), 2.80 (4H), 2.75 (2H), 2.44 (4H), 1.60 (4H), 1.38 (2H); m/z (M+H)=385.31.

Example 22

Preparation of 3-(2-morpholin-4-yl-ethyl)-imidazo[1,5-a]pyridine-1-carboxylic acid (3-chloro-phenyl)-amide

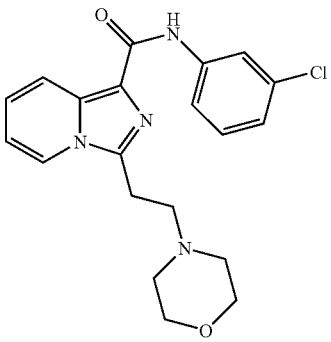

To a solution of 3-chloroaniline (0.060 mL, 0.54 mmol) and triethylamine (0.16 mL, 1.14 mmol) in CH₂Cl₂ (10 mL) was added 3-(2-morpholin-4-yl-ethyl)-imidazo[1,5-a]pyridine-1-carbonyl chloride hydrochloride (150 mg, 0.45 mmol). The mixture was stirred at ambient temperature for 1 h then washed with sat. aq. NaHCO₃ (20 mL). The organic layer was separated and the aqueous layer was extracted with dichloromethane (20 mL). The combined organic layers were dried over anhydrous sodium sulfate and concentrated in vacuo. The residue was chromatographed on silica to yield the title compound (61 mg, 35%). ¹H NMR (DMSO-$d_6$) δ 10.0 (1H), 8.45 (1H), 8.15 (2H), 7.81 (1H), 7.35 (1H), 7.20 (1H), 7.10 (1H), 6.94 (1H), 3.49 (4H), 3.26 (2H), 2.81 (2H), 2.44 (4H); m/z (M+H)=385.18.

Example 23

Preparation of morpholin-4-yl-[3-(2-morpholin-4-yl-ethyl)-imidazo[1,5-a]pyridin-1-yl]-methanone

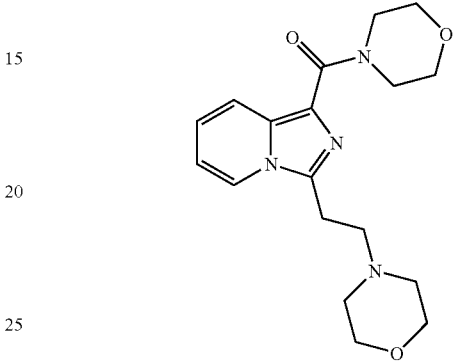

To a solution of morpholine (0.050 mL, 0.54 mmol) and triethylamine (0.16 mL, 1.14 mmol) in CH₂Cl₂ (10 mL) was added 3-(2-morpholin-4-yl-ethyl)-imidazo[1,5-a]pyridine-1-carbonyl chloride hydrochloride (150 mg, 0.45 mmol). The mixture was stirred at ambient temperature for 1 h then washed with sat. aq. NaHCO₃ (20 mL). The organic layer was separated and the aqueous layer was extracted with dichloromethane (20 mL). The combined organic layers were dried over anhydrous sodium sulfate and concentrated in vacuo. The residue was chromatographed on silica to yield the title compound (85 mg, 55%). ¹H NMR (DMSO-$d_6$) δ 8.35 (1H), 8.05 (1H), 7.08 (1H), 6.85 (1H), 3.65 (4H), 4.05 (4H), 3.53 (4H), 3.18 (2H), 2.75 (2H), 2.45 (4H); m/z (M+H)=345.21.

Example 24

Preparation of 3-(2-morpholin-4-yl-ethyl)-imidazo[1,5-a]pyridine-1-carboxylic acid 4-chloro-benzylamide

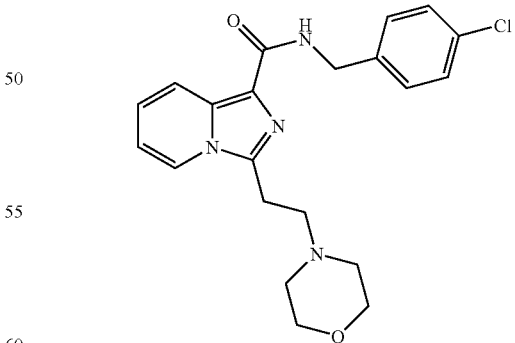

To a solution of 4-chlorobenzylamine (0.080 mL, 0.54 mmol) and triethylamine (0.16 mL, 1.14 mmol) in CH₂Cl₂ (10 mL) was added 3-(2-morpholin-4-yl-ethyl)-imidazo[1,5-a]pyridine-1-carbonyl chloride hydrochloride (150 mg, 0.45 mmol). The mixture was stirred at ambient temperature for 1 h then washed with sat. aq. NaHCO₃ (20 mL). The organic layer was separated and the aqueous layer was extracted with dichloromethane (20 mL). The combined organic layers were dried over anhydrous sodium sulfate and concentrated in vacuo. The residue was chromatographed on silica to yield the title compound (85 mg, 47%). $^1$H NMR (DMSO-$_{d6}$) δ 8.52 (1H), 8.35 (1H), 8.05 (1H), 7.35 (4H), 7.08 (1H), 6.85 (1H), 4.45 (2H), 3.58 (4H), 3.20 (2H), 2.78 (2H), 2.45 (4H); m/z (M+H)=399.16.

Example 25

Preparation of 3-(2-morpholin-4-yl-ethyl)-imidazo[1,5-a]pyridine-1-carboxylic acid methyl-phenyl-amide

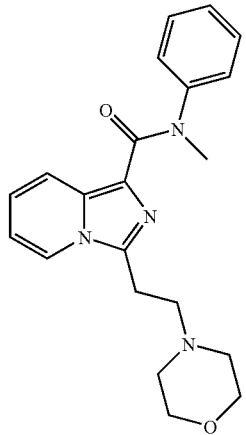

To a solution of n-methylaniline (0.060 mL, 0.54 mmol) and triethylamine (0.16 mL, 1.14 mmol) in CH$_2$Cl$_2$ (10 mL) was added 3-(2-morpholin-4-yl-ethyl)-imidazo[1,5-a]pyridine-1-carbonyl chloride hydrochloride (150 mg, 0.45 mmol). The mixture was stirred at ambient temperature for 1 h then washed with sat. aq. NaHCO$_3$ (20 mL). The organic layer was separated and the aqueous layer was extracted with dichloromethane (20 mL). The combined organic layers were dried over anhydrous sodium sulfate and concentrated in vacuo. The residue was chromatographed on silica to yield the title compound (105 mg, 64%). $^1$H NMR (DMSO-$_{d6}$) δ 8.23 (1H), 8.00 (1H), 7.30 (2H), 7.19 (3H), 7.05 (1H), 6.81 (1H), 3.52 (4H), 3.48 (3H), 2.95 (2H), 2.45 (2H), 2.33 (4H); m/z (M+H)=365.26.

Example 26

Preparation of 3-(2-morpholin-4-yl-ethyl)-imidazo[1,5-a]pyridine-1-carboxylic acid bicyclo[2.2.1]hept-2-ylamide

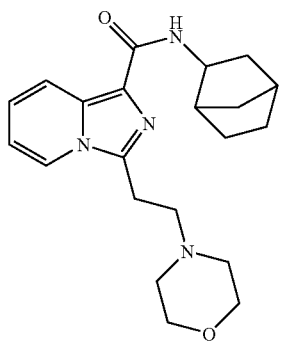

To a solution of exo-2-amino-norbornane (0.064 mL, 0.54 mmol) and triethylamine (0.16 mL, 1.14 mmol) in CH$_2$Cl$_2$ (10 mL) was added 3-(2-morpholin-4-yl-ethyl)-imidazo[1,5-a]pyridine-1-carbonyl chloride hydrochloride (150 mg, 0.45 mmol). The mixture was stirred at ambient temperature for 1 h then washed with sat. aq. NaHCO$_3$ (20 mL). The organic layer was separated and the aqueous layer was extracted with dichloromethane (20 mL). The combined organic layers were dried over anhydrous sodium sulfate and concentrated in vacuo. The residue was chromatographed on silica to yield the title compound (78 mg, 47%). $^1$H NMR (DMSO-$_{d6}$) δ 8.33 (1H), 8.05 (1H), 7.35 (1H), 7.05 (1H), 6.83 (1H), 3.75 (1H), 3.55 (4H), 3.90 (2H), 2.75 (2H), 2.40 (4H), 2.25 (1H), 2.18 (1H), 1.68 (1H), 1.48 (4H), 1.15 (3H); m/z (M+H)= 369.22.

Example 27

Preparation of 3-(2-morpholin-4-yl-ethyl)-imidazo[1,5-a]pyridine-1-carboxylic acid (3-fluoro-phenyl)-amide

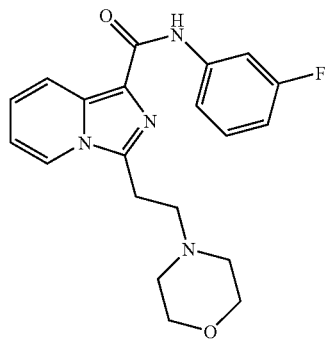

To a solution of 3-fluoroaniline (0.052 mL, 0.54 mmol) and triethylamine (0.16 mL, 1.14 mmol) in CH$_2$Cl$_2$ (10 mL) was added 3-(2-morpholin-4-yl-ethyl)-imidazo[1,5-a]pyridine-1-carbonyl chloride hydrochloride (150 mg, 0.45 mmol). The mixture was stirred at ambient temperature for 1 h then washed with sat. aq. NaHCO$_3$ (20 mL). The organic layer was separated and the aqueous layer was extracted with dichloromethane (20 mL). The combined organic layers were dried over anhydrous sodium sulfate and concentrated in vacuo. The residue was chromatographed on silica to yield the title compound (30 mg, 18%). $^1$H NMR (DMSO-$_{d6}$) δ 10.02 (1H), 8.45 (1H), 8.15 (1H), 7.88 (1H), 7.70 (1H), 7.43 (1H), 7.20 (1H), 6.95 (1H), 6.85 (1H), 3.58 (4H), 3.25 (2H), 2.80 (2H), 2.44 (4H); m/z (M+H)=369.22.

Example 28

Preparation of 3-(2-morpholin-4-yl-ethyl)-imidazo[1,5-a]pyridine-1-carboxylic acid pyridin-3-ylamide

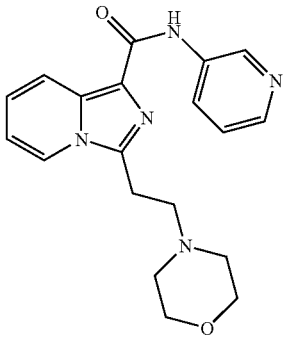

To a solution of 3-aminopyridine (0.051 g, 0.54 mmol) and triethylamine (0.16 mL, 1.14 mmol) in CH$_2$Cl$_2$ (10 mL) was added 3-(2-morpholin-4-yl-ethyl)-imidazo[1,5-a]pyridine-1-carbonyl chloride hydrochloride (150 mg, 0.45 mmol). The mixture was stirred at ambient temperature for 1 h then washed with sat. aq. NaHCO$_3$ (20 mL). The organic layer was separated and the aqueous layer was extracted with dichloromethane (20 mL). The combined organic layers were dried over anhydrous sodium sulfate and concentrated in vacuo. The residue was chromatographed on silica to yield the title compound (50 mg, 32%). $^1$H NMR (DMSO-$_{d6}$) δ 10.05 (1H), 9.05 (1H), 8.45 (1H), 8.28 (2H), 8.15 (1H), 7.35 (1H), 7.20 (1H), 6.94 (1H), 3.58 (4H), 3.26 (2H), 2.80 (2H), 2.45 (4H); m/z (M+H)=352.17.

Example 29

Preparation of 3-(2-morpholin-4-yl-ethyl)-imidazo[1,5-a]pyridine-1-carboxylic acid (pyridin-3-ylmethyl)-amide

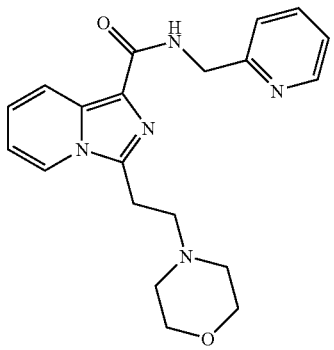

To a solution of 2-(aminomethyl)pyridine (0.052 g, 0.54 mmol) and triethylamine (0.16 mL, 1.14 mmol) in CH$_2$Cl$_2$ (10 mL) was added 3-(2-morpholin-4-yl-ethyl)-imidazo[1,5-a]pyridine-1-carbonyl chloride hydrochloride (150 mg, 0.45 mmol). The mixture was stirred at ambient temperature for 1 h then washed with sat. aq. NaHCO$_3$ (20 mL). The organic layer was separated and the aqueous layer was extracted with dichloromethane (20 mL). The combined organic layers were dried over anhydrous sodium sulfate and concentrated in vacuo. The residue was chromatographed on silica to yield the title compound (52 mg, 32%). $^1$H NMR (DMSO-$_{d6}$) δ 8.50 (2H), 8.35 (1H), 8.05 (1H), 7.54 (1H), 7.32 (1H), 7.25 (1H), 78.08 (1H), 6.85 (1H), 4.59 (2H), 3.57 (4H), 3.20 (2H), 2.80 (2H), 2.43 (4H); m/z (M+H)=366.15.

Example 30

Preparation of 3-(2-morpholin-4-yl-ethyl)-imidazo[1,5-a]pyridine-1-carboxylic acid naphthalen-1-ylamide

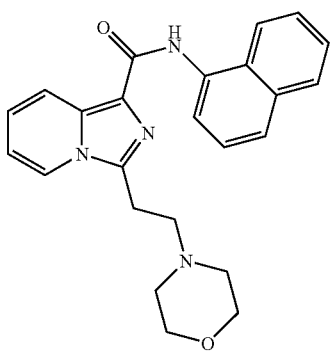

To a solution of 1-naphylamine (0.077 g, 0.54 mmol) and triethylamine (0.16 mL, 1.14 mmol) in CH$_2$Cl$_2$ (10 mL) was added 3-(2-morpholin-4-yl-ethyl)-imidazo[1,5-a]pyridine-1-carbonyl chloride hydrochloride (150 mg, 0.45 mmol). The mixture was stirred at ambient temperature for 1 h then washed with sat. aq. NaHCO$_3$ (20 mL). The organic layer was separated and the aqueous layer was extracted with dichloromethane (20 mL). The combined organic layers were dried over anhydrous sodium sulfate and concentrated in vacuo. The residue was chromatographed on silica to yield the title compound (58 mg, 32%). $^1$H NMR (DMSO-$_{d6}$) δ 10.0 (1H), 8.45 (1H), 8.10 (1H), 7.98 (3H), 7.78 (1H), 7.55 (3H), 7.18 (1H), 6.93 (1H), 3.59 (4H), 3.30 (2H), 2.85 (2H), 2.57 (4H); m/z (M+H)=401.13.

Example 31

Preparation of 3-(2-morpholin-4-yl-ethyl)-imidazo[1,5-a]pyridine-1-carboxylic acid (3,5-dimethyl-tricyclo[3.3.1.1$^{3,7}$]decan-1-yl)-amide

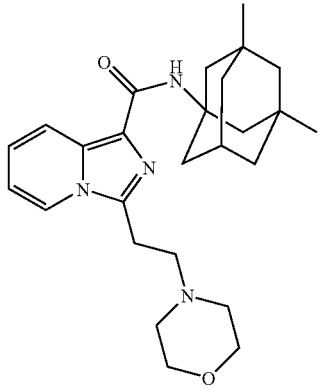

To a solution of 3-butyl-imidazo[1,5-a]pyridine-1-carboxylic acid (200 mg, 0.73 mmol) in DMF (5 mL) was added EDC (182 mg, 0.95 mmol), HOBt, (129 mg, 0.95 mmol) and iPr$_2$EtN (0.22 mL, 1.31 mmol). The mixture was allowed to stir for 10 min. and 3,5-dimethyl-1-aminoadamantane hydrochloride (187 mg, 0.88 mmol) was added. The mixture was stirred for 15 h then diluted with ethyl acetate (30 mL) and washed with water (50 mL). The organic layer was dried over anhydrous sodium sulfate and concentrated in vacuo. The residue was chromatographed on silica to yield the title compound (50 mg, 16%). $^1$H NMR (DMSO-$_{d6}$) δ 8.32 (1H), 8.00 (1H), 7.05 (1H), 6.95 (1H), 6.81 (1H), 3.55 (4H), 3.15 (2H), 2.73 (2H), 2.45 (4H), 2.11 (1H), 1.90 (2H), 1.73 (4H), 1.30 (4H), 1.75 (2H), 0.85 (6H); m/z (M+H)=437.22.

Example 32

Preparation of 3-(2-morpholin-4-yl-ethyl)-imidazo[1,5-a]pyridine-1-carboxylic acid phenylamide

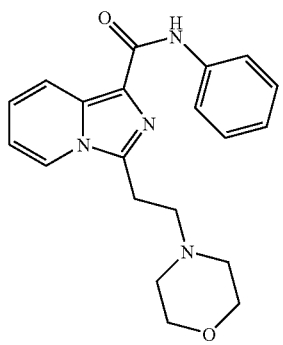

To a solution of 3-butyl-imidazo[1,5-a]pyridine-1-carboxylic acid (200 mg, 0.73 mmol) in DMF (5 mL) was added EDC (182 mg, 0.95 mmol), HOBt, (129 mg, 0.95 mmol) and iPr$_2$EtN (0.22 mL, 1.31 mmol). The mixture was allowed to stir for 10 min. and aniline (0.080 mL, 0.88 mmol) was added. The mixture was stirred for 15 h then diluted with ethyl acetate (30 mL) and washed with water (50 mL). The organic layer was dried over anhydrous sodium sulfate and concentrated in vacuo. The residue was chromatographed on silica to yield the title compound (40 mg, 16%). $^1$H NMR (DMSO-$d_6$) δ 9.72 (1H), 8.41 (1H), 8.15 (1H), 7.83 (2H), 7.30 (2H), 7.18 (1H), 7.05 (1H), 6.95 (1H), 3.58 (4H), 3.25 (2H), 2.80 (2H), 2.48 (4H); m/z (M+H)=351.15.

Example 33

Preparation of 3-(2-morpholin-4-yl-ethyl)-imidazo[1,5-a]pyridine-1-carboxylic acid benzylamide

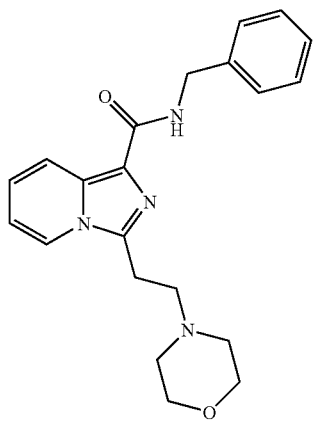

To a solution of 3-butyl-imidazo[1,5-a]pyridine-1-carboxylic acid (200 mg, 0.73 mmol) in DMF (5 mL) was added EDC (182 mg, 0.95 mmol), HOBt, (129 mg, 0.95 mmol) and iPr$_2$EtN (0.22 mL, 1.31 mmol). The mixture was allowed to stir for 10 min. and benzylamine (0.096 mL, 0.88 mmol) was added. The mixture was stirred for 15 h then diluted with ethyl acetate (30 mL) and washed with water (50 mL). The organic layer was dried over anhydrous sodium sulfate and concentrated in vacuo. The residue was chromatographed on silica to yield the title compound (45 mg, 17%). $^1$H NMR (DMSO-$d_6$) δ 8.43 (1H), 8.28 (1H), 8.07 (1H), 7.26 (4H), 7.20 (1H), 7.05 (1H), 6.85 (1H), 4.44 (2H), 3.48 (4H), 3.20 (2H), 2.80 (2H), 2.45 (4H); m/z (M+H)=365.13.

Competition Binding Assay (96 Well Filtration)

3H-CP-55940 (Perkin-Elmer, NET-1051) was selected and used as the radio-labelled tracer for this study. CP55940 (Tocris, 0949) was selected and used as the unlabelled competitors for this study.

Materials

Assay buffer: 50 mM Tris-HCl pH 7.4, 2.5 mM EDTA, 0.5% protease free BSA

Filtration buffer: 50 mM Tris-HCl pH 7.4, 2.5 mM EDTA, 0.5% protease free BSA

Membranes: Thawed on ice and diluted to give 10 μg/ml (0.2 μg/20 μl), kept on ice.

Radioligand: [$^3$H]CP 55,940 (Perkin Elmer, NET-1051, 160.6 Ci/mmol), diluted in assay buffer to give 1.61 μCi/ml, ~89133 dpm/25 μl. Final assay concentration 1.0 nM.

Ligand: CP 55,940 (Tocris, 0949), diluted in assay buffer.

Filters: GF/B Unifilter plate (Perkin Elmer, 6005177) presoaked in 0.5% PEI for 2 h at RT.

Assay Procedure

180 μl of assay buffer (205 μl for total binding determination), 25 μl of ligand at increasing concentrations, 25 μl of radioligand, 20 μl of membrane extracts (0.2 μg) were added successively in the wells of a 96-well plate (Master Block, Greiner, 786201) and incubated 60 min at 30° C. in a water bath. This was then filtered over GF/B filters with a Filtermate Harvester (Perkin Elmer) and the filters were washed six times with 0.5 ml of ice-cold filtration buffer. 50 μl of Microscint 20 (Packard) was added, incubated 15 min on an orbital shaker and counted with a TopCount™ or MicroBeta™ for 1 min/well.

The compounds of the present invention typically show binding activities of >50% at 10 μM concentration. For example, the compounds of Examples 1, 2, 6-9, 12-14, 17, 18 and 20 exhibit binding affinities of >60% at 10 μM.

The entire disclosures of all applications, patents and publications, cited above and below, are hereby incorporated by reference.

While the invention has been depicted and described by reference to exemplary embodiments of the invention, such a reference does not imply a limitation on the invention, and no such limitation is to be inferred. The invention is capable of considerable modification, alteration, and equivalents in form and function, as will occur to those ordinarily skilled in the pertinent arts having the benefit of this disclosure. The depicted and described embodiments of the invention are exemplary only, and are not exhaustive of the scope of the invention. Consequently, the invention is intended to be limited only by the spirit and scope of the appended claims, giving full cognizance to equivalence in all respects.

What is claimed is:

1. A compound of formula I:

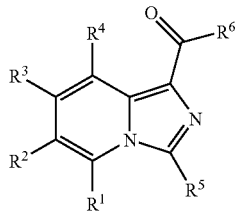

wherein

R$^1$, R$^2$, R$^3$ and R$^4$ are each independently hydrogen, halogen, hydroxyl, cyano, nitro, amino, alkylamino, dialkylamino, carboxyl, alkyl, alkenyl, alkynyl, aryl, arylalkyl, heteroaryl, heteroarylalkyl, heterocycle, heterocyclealkyl, cycloalkyl, aroyl, acyl, alkoxy, aryloxy, alkythio, arylthio, alkoxycarbonyl or aryloxycarbonyl;

R$^5$ is alkyl, aryl or heterocyclealkyl;

R$^6$ is hydroxyl, alkyl, halogenated alkyl, alkenyl, alkynyl, aryloxy, aryl, arylalkyl, heteroaryl, heteroarylalkyl, heterocycle, heterocyclealkyl or NR$^7$R$^8$;

R$^7$ and R$^8$ are each independently, hydrogen, alkyl, aryl, cycloalkyl, cycloalkylalkyl, arylalkyl, heteroaryl, heteroarylalkyl, heterocycle, or heterocyclealkyl;

and pharmaceutically acceptable salts thereof;

with the provisos that:

(i) R$^6$ is other than 1-methyl-2-[4-(2-pyrimidinyl)-1-piperazinyl]ethyl;

(ii) when R$^6$ is 2-pyridinyl, then R$^5$ is other than phenyl, chlorophenyl, fluorophenyl, nitrophenyl, methoxyphenyl or alkyl substituted phenyl;

(iii) when R$^5$ is alkyl, R$^6$ is NR$^7$R$^8$ and one of R$^7$ and R$^8$ is hydrogen, then the other of R$^7$ and R$^8$ is not hexahydropyrrolizinylmethyl, hexahydro-1H-2,5-methanocyclopenta[c]pyrrolyl, azabicyclo [2.2.2]oct-3-yl, 8-methyl-8-azabicyclo[3.2.1]-oct-3-yl or 9-methyl-9-azabicyclo[3.3.1]-non-3-yl;

(iv) when R$^6$ is OH, then R$^5$ is other than phenyl, ethyl, CF$_3$, or isobutyl, and said compound is not 2,2,2-trifluoro-1-[3-(4-nitrophenyl)imidazo[1,5-a]pyridine-1-yl-ethanone, phenyl(3-phenylimidazo[1,5-a]pyridine-1-yl-methanone, 1-[3-(4-chlorophenyl)imidaz[1,5-a]pyridine-1-yl]-1-propanone, or 1-(3-methylimidazo[1,5-a]pyridine-1-yl)ethanone.

2. A compound according to claim 1 wherein

R$^1$, R$^2$, R$^3$ and R$^4$ are hydrogen;

R$^5$ is alkyl, aryl or heterocyclealkyl;

R$^6$ is hydroxyl, alkyl, halogenated alkyl, aryl, heterocycle, or NR$^7$R$^8$; and R$^7$ and R$^8$ are each independently, hydrogen, alkyl, cycloalkyl, aryl, arylalkyl, heteroaryl, heteroarylalkyl, or heterocycle.

3. A compound of formula I:

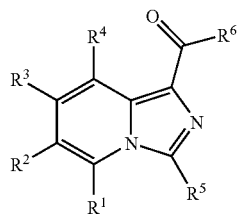

wherein:

R$^1$, R$^2$, R$^3$ and R$^4$ are each independently hydrogen, halogen, hydroxyl, cyano, nitro, amino, carboxyl, alkyl, alkenyl, or aryl;

R$^5$ is alkyl, naphthalene, or —(CH$_2$)$_n$-A,

R$^6$ is alkyl, CF$_3$, hydroxyl, naphthalene, A, —NH—(CH$_2$)$_m$-A, —N(CH$_3$)(CH$_2$)$_m$-A, —NH—(CH$_2$)$_m$—B, or —N(CH$_3$)(CH$_2$)$_m$—B;

n=1, 2 or 3;

m=0, 1, 2 or 3;

A is represented by:

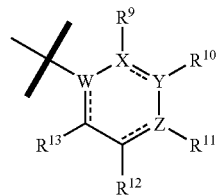

wherein each ----- independently represents a single or double bond;

R$^9$, R$^{10}$, R$^{11}$, R$^{12}$ and R$^{13}$ are each independently H, halogen, alkyl or NO$_2$, W, X, Y and Z are each independently C, O or N; and B is norborane, naphthalene, adamantane or 1,3-dimethyl adamantane;

and pharmaceutically acceptable salts thereof;

with the provisos:

(i) when R$^5$ is —(CH$_2$)$_n$-A and A is optionally substituted phenyl, then n is other than 1;

(ii) when R$^6$ is hydroxyl and R$^1$-R$^4$ are hydrogen, then R$^5$ is other than ethyl, iso-butyl or CF$_3$;

and said compound is not 1-(3-methylimidazo[1,5-a]pyridine-1-yl)ethanone.

4. A compound according to formula II:

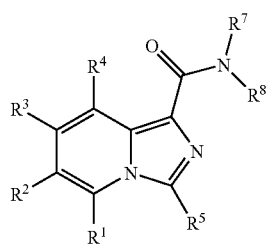

wherein

R$^1$ through R$^4$ are each independently hydrogen, halogen, hydroxy, cyano, nitro, amino, carboxyl, alkyl, alkenyl, or aryl;

$R^5$ is hydrogen, alkyl, naphthalene or —$(CH_2)_n$-A, wherein n=0, 1, 2 or 3;

$R^7$ and $R^8$ are each individually hydrogen, alkyl, naphthalene, A, B, -alkylene-A or -alkylene-B;

wherein A is represented by:

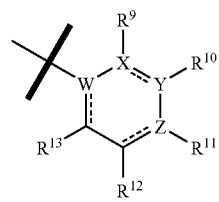

wherein each ----- independently represents a single or double bond;

$R^9$ through $R^{13}$ are each independently hydrogen, halogen, alkyl or $NO_2$, W, X, Y, and Z are each independently C, O and N; and B is norborane, naphthalene, adamantane or 1,3-dimethyl adamantane;

and pharmaceutically acceptable salts thereof;

with the proviso that $R^5$ is other than 4-trifluoromethyl-3-pyridinyl.

5. A compound according to claim 1, wherein $R^1$, $R^2$, $R^3$ and $R^4$ are independently hydrogen, halogen, hydroxy, cyano, nitro, amino, carboxyl, alkyl, alkenyl, or aryl.

6. A compound according to claim 1 wherein $R^1$, $R^2$, $R^3$ and $R^4$ are hydrogen.

7. A compound according to claim 3, wherein W, X, Y and Z are C.

8. A compound according to claim 3, wherein one of W, X, Y and Z is N and the remainder are C.

9. A compound according to claim 3, where each ---- represents a single bond.

10. A compound according to claim 1, wherein $R^5$ is naphthalenyl, butyl, propyl or morpholinylethyl.

11. A compound according to claim 1, wherein $R^6$ is hydroxyl, alkyl, halogenated alkyl, optionally substituted phenyl, optionally substituted naphthalenyl, optionally substituted morpholinyl or $NR^7R^8$.

12. A compound according to claim 1, wherein $R^7$ and $R^8$ are each independently, hydrogen, alkyl, cycloalkyl, optionally substituted phenyl, optionally substituted naphthalenyl, optionally substituted benzyl, optionally substituted pyridinyl, optionally substituted pyridinylmethyl or optionally substituted piperidinyl.

13. A compound according to claim 1, wherein $R^6$ is hydroxyl, unsubstituted alkyl, substituted alkyl, iodophenyl, naphthalenyl, —NH-adamantan-1-yl, iodonitrophenyl, —NH-piperidinyl, —NH-chlorophenyl, morpholinyl, —NH-chlorobenzyl, —N(CH_3)phenyl, —NH-bicyclo[2.2.1]heptyl, —NH-fluorophenyl, —NH-pyridinyl, —NH-pyridinylmethyl, —NH-naphthalenyl, —NH-3,5-dimethyltricyclo[3.3.1.1$^{3,7}$]decanyl, —NH-phenyl, or —NH-benzyl.

14. A compound according to claim 1 wherein $R^1$-$R^4$ are hydrogen, $R^5$ is aryl, $R^6$ is hydroxyl, alkyl, halogenated alkyl, optionally substituted aryl or $NR^7R^8$, and $R^7$ and $R^8$ are independently hydrogen or cycloalkyl.

15. A compound according to claim 1 wherein $R^1$-$R^4$ are hydrogen, $R^5$ is alkyl, $R^6$ is hydroxyl, halogenated alkyl, optionally substituted naphthalenyl, optionally substituted phenyl or $NR^7R^8$, and $R^7$ and $R^8$ are independently hydrogen or cycloalkyl.

16. A compound according to claim 1 wherein $R^1$-$R^4$ are hydrogen, $R^5$ is heterocyclealkyl, $R^6$ is halogenated alkyl, optionally substituted aryl, heteroaryl, heterocycle or $NR^7R^8$, and $R^7$ and $R^8$ are independently hydrogen, alkyl, optionally substituted aryl, cyclooalkyl, heterocycle, arylalkyl, or heteroarylalkyl.

17. A compound according to claim 1 chosen from:

1-(3-naphthalen-1-yl-imidazo[1,5-a]pyridin-1-yl)-butan-1-one, (2-iodo-phenyl)-(3-naphthalen-1-yl-imidazo[1,5-a]pyradin-1-yl)-methanone, 2,2,2-trifluoro-1-(3-naphthalen-1-yl-imidazo[1,5-a]pyradin-1-yl)-ethanone, 3-naphthalen-1-yl-imidazo[1,5-a]pyradine-1-carboxylic acid, 3-naphthalen-1-yl-imidazo[1,5-a]pyradine-1-carboxylic acid adamantan-1-ylamide, 3-butyl-imidazo[1,5-a]pyradin-1-yl-naphthalen-1-yl-methanone, (3-butyl-imidazo[1,5-a]pyradin-1-yl)-(2-iodo-phenyl)-methanone, 3-butyl-imidazo[1,5-a]pyradin-1-yl)-2(2-iodo-5-nitro-phenyl)-methanone, 1-(3-butyl-imidazo[1,5-a]pyradin-1-yl)-2,2,2-trifluoro-ethanone, 3-butyl-imidazo[1,5-a]pyradine-1-carboxylic acid, 3-butyl-imidazo[1,5-a]pyradine-1-carboxylic acid adamantan-1-ylamide, 3-propyl-imidazo[1,5-a]pyradin-1-yl-naphthalen-1-yl-methanone, (2-iodo-phenyl)-(3-propyl-imidazo[1,5-a]pyradin-1-yl)-methanone, 2,2,2-trifluoro-1-(3-propyl-imidazo[1,5-a]pyradin-1-yl)-ethanone, 3-propyl-imidazo[1,5-a]pyradine-1-carboxylic acid, 3-propyl-imidazo[1,5-a]pyradine-1-carboxylic acid adamantan-1-ylamide,

[3-(2-morpholin-4-yl-ethyl)-imidazo[1,5-a]pyradin-1-yl]-naphthalen-1-yl-methanone, (2-iodo-phenyl)-[3-(2-morpholin-4-yl-ethyl)-imidazo[1,5-a]pyridin-1-yl]-methanone, 2,2,2-trifluoro-1-[3-(2-morpholin-4-yl-ethyl)-imidazo[1,5-a]pyridin-1-yl]-ethanone, 3-(2-morpholin-4-yl-ethyl)-imidazo[1,5-a]pyradine-1-carboxylic acid adamantan-1-ylamide, 3-(2-morpholin-4-yl-ethyl)-imidazo[1,5-a]pyradine-1-carboxylic acid piperidin-1-ylamide, 3-(2-morpholin-4-yl-ethyl)-imidazo[1,5-a]pyradine-1-carboxylic acid (3-chloro-phenyl)-amide, morpholin-4-yl-[3-(2-morpholin-4-yl-ethyl)-imidazo[1,5-a]pyridin-1-yl]-methanone, 3-(2-morpholin-4-yl-ethyl)-imidazo[1,5-a]pyradine-1-carboxylic acid 4-chloro-benzylamide, 3-(2-morpholin-4-yl-ethyl)-imidazo[1,5-a]pyradine-1-carboxylic acid methyl-phenyl-amide, 3-(2-morpholin-4-yl-ethyl)-imidazo[1,5-a]pyradine-1-carboxylic acid bicyclo[2.2.1]hept-2-ylamide, 3-(2-morpholin-4-yl-ethyl)-imidazo[1,5-a]pyradine-1-carboxylic acid (3-fluoro-phenyl)-amide, 3-(2-morpholin-4-yl-ethyl)-imidazo[1,5-a]pyradine-1-carboxylic acid pyridin-3-ylamide, 3-(2-morpholin-4-yl-ethyl)-imidazo[1,5-a]pyradine-1-carboxylic acid (pyridin-3-ylmethyl)-amide, 3-(2-morpholin-4-yl-ethyl)-imidazo[1,5-a]pyradine-1-carboxylic acid naphthalen-1-ylamide, 3-(2-morpholin-4-yl-ethyl)-imidazo[1,5-a]pyradine-1-carboxylic acid (3,5-dimethyl-tricyclo[3.3.1.1$^{3,7}$]decan-1-yl)-amide, 3-(2-morpholin-4-yl-ethyl)-imidazo[1,5-a]pyradine-1-carboxylic acid phenylamide, 3-(2-morpholin-4-yl-ethyl)-imidazo[1,5-a]pyradine-1-carboxylic acid benzylamide, and pharmaceutically acceptable salts thereof, wherein if the compound exhibits chirality it can be in the form of a mixture of enantiomers such as a racemate or a mixture of diastereomers, or can be in the form of a single enantiomer or a single diastereomer.

18. A pharmaceutical composition comprising a compound according to claim 1 and a pharmaceutically acceptable carrier.

19. A method of treating a patient with a condition selected from the group consisting of chronic pain, an inflammatory disorder, rheumatoid arthritis, multiple sclerosis, osteoporosis and osteoarthritis comprising administering to the patient in need of such treatment a therapeutically effective amount of a compound according to claim 1.

20. The method according to claim 19, wherein the condition is an inflammatory disorder.

21. The method according to claim 19, wherein the condition is chronic pain.

22. The method according to claim 19, wherein the condition is rheumatoid arthritis.

23. The method according to claim 19, wherein the condition is osteoarthritis.

24. The method according to claim 19, wherein the condition is osteoporosis.

* * * * *